(12) United States Patent
Theiss et al.

(10) Patent No.: US 10,617,434 B2
(45) Date of Patent: Apr. 14, 2020

(54) METHODS AND DEVICES FOR POSITIONING A PATIENT-SPECIFIC ACETABULUM REAMING AND CUP POSITIONING GUIDE

(71) Applicant: INOVA HEALTH SYSTEM, Falls Church, VA (US)

(72) Inventors: Mark Theiss, Fairfax, VA (US); Jihui Li, Burke, VA (US)

(73) Assignee: INOVA HEALTH SYSTEM, Falls Church, VA (US)

( * ) Notice: Subject to any disclaimer, the term of this patent is extended or adjusted under 35 U.S.C. 154(b) by 97 days.

(21) Appl. No.: 16/035,049

(22) Filed: Jul. 13, 2018

(65) Prior Publication Data

US 2019/0008531 A1  Jan. 10, 2019

Related U.S. Application Data

(63) Continuation of application No. 15/630,274, filed on Jun. 22, 2017, now Pat. No. 10,022,137, which is a continuation of application No. 14/321,925, filed on Jul. 2, 2014, now Pat. No. 9,693,785.

(60) Provisional application No. 61/841,964, filed on Jul. 2, 2013.

(51) Int. Cl.
| | |
|---|---|
| *A61F 5/00* | (2006.01) |
| *A61B 17/17* | (2006.01) |
| *A61F 2/46* | (2006.01) |
| *A61B 17/56* | (2006.01) |
| *A61F 2/30* | (2006.01) |

(52) U.S. Cl.
CPC ........ *A61B 17/175* (2013.01); *A61B 17/1746* (2013.01); *A61F 2/4609* (2013.01); *A61B 2017/568* (2013.01); *A61F 2/30942* (2013.01); *A61F 2002/4687* (2013.01)

(58) Field of Classification Search
CPC combination set(s) only.
See application file for complete search history.

(56) References Cited

U.S. PATENT DOCUMENTS

| | | |
|---|---|---|
| 8,808,302 B2 | 8/2014 | Roose |
| 2010/0049195 A1 | 2/2010 | Park et al. |
| 2012/0041445 A1 | 2/2012 | Roose et al. |
| 2016/0038161 A1* | 2/2016 | Gibson ............... A61F 2/30942 606/91 |

FOREIGN PATENT DOCUMENTS

WO   2012/010366 A1   1/2012

* cited by examiner

*Primary Examiner* — Sameh R Boles
(74) *Attorney, Agent, or Firm* — J.A. Lindeman & Co. PLLC

(57) ABSTRACT

A method and a device for use in total hip arthroplasty surgery is provided. The device includes a first guide member which includes a body having a top surface and a bottom surface, a plurality of first guide legs protruding from the body, and a plurality of protrusions extending from the body. The plurality of first guide legs include a contact area disposed on the open end of the first guide leg. The device also includes a third guide member which includes a tube, a plate configured to engage with the first guide member, and a plurality of holes disposed on the plate configured to receive the plurality of protrusions of the first guide member to couple the first guide member with the third guide member.

17 Claims, 25 Drawing Sheets

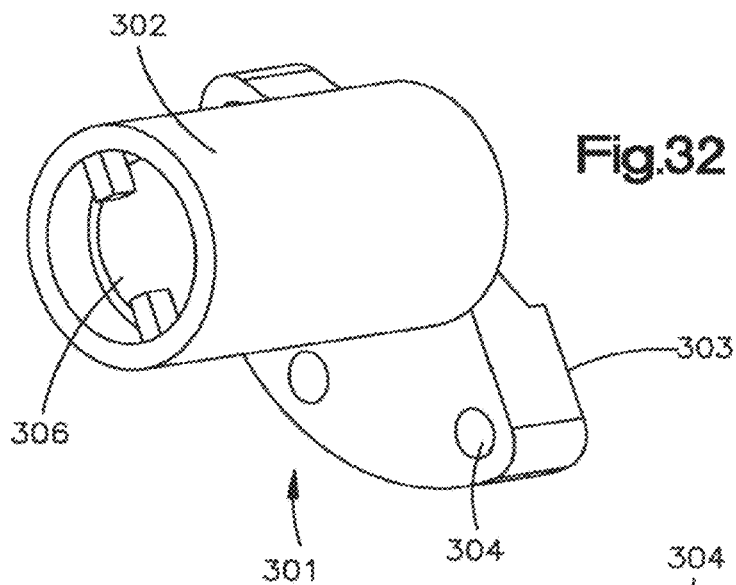
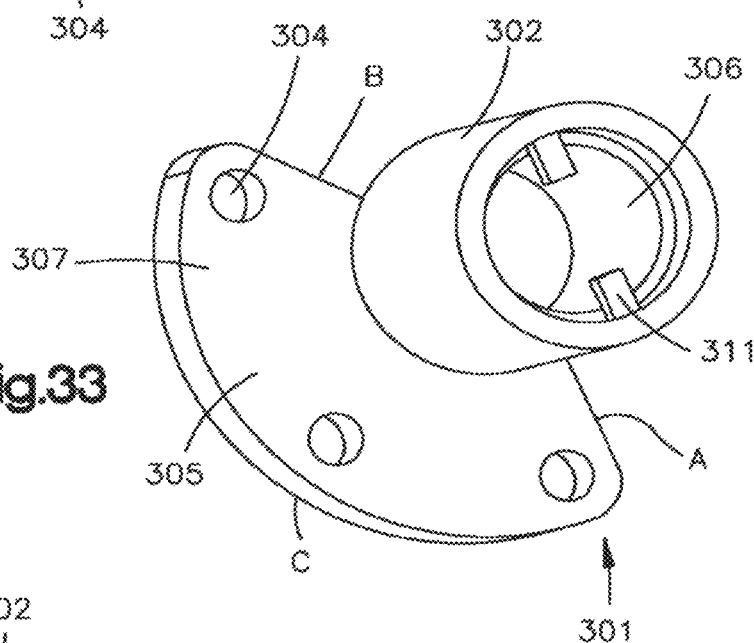
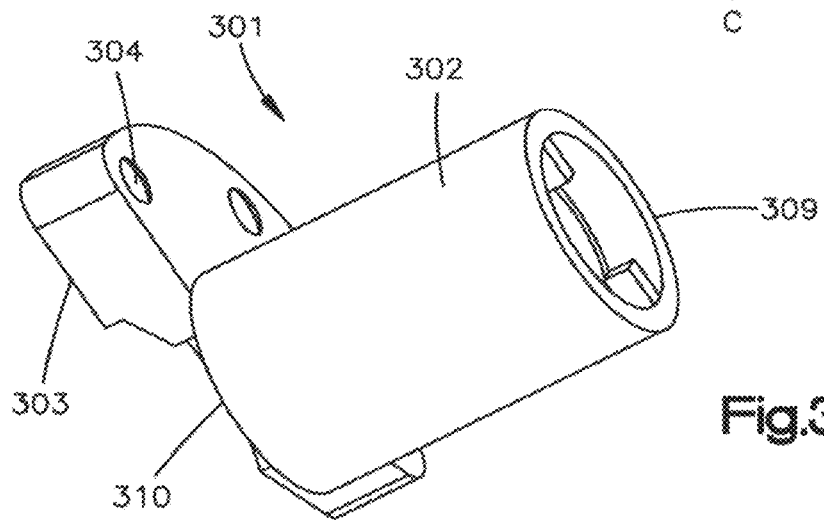

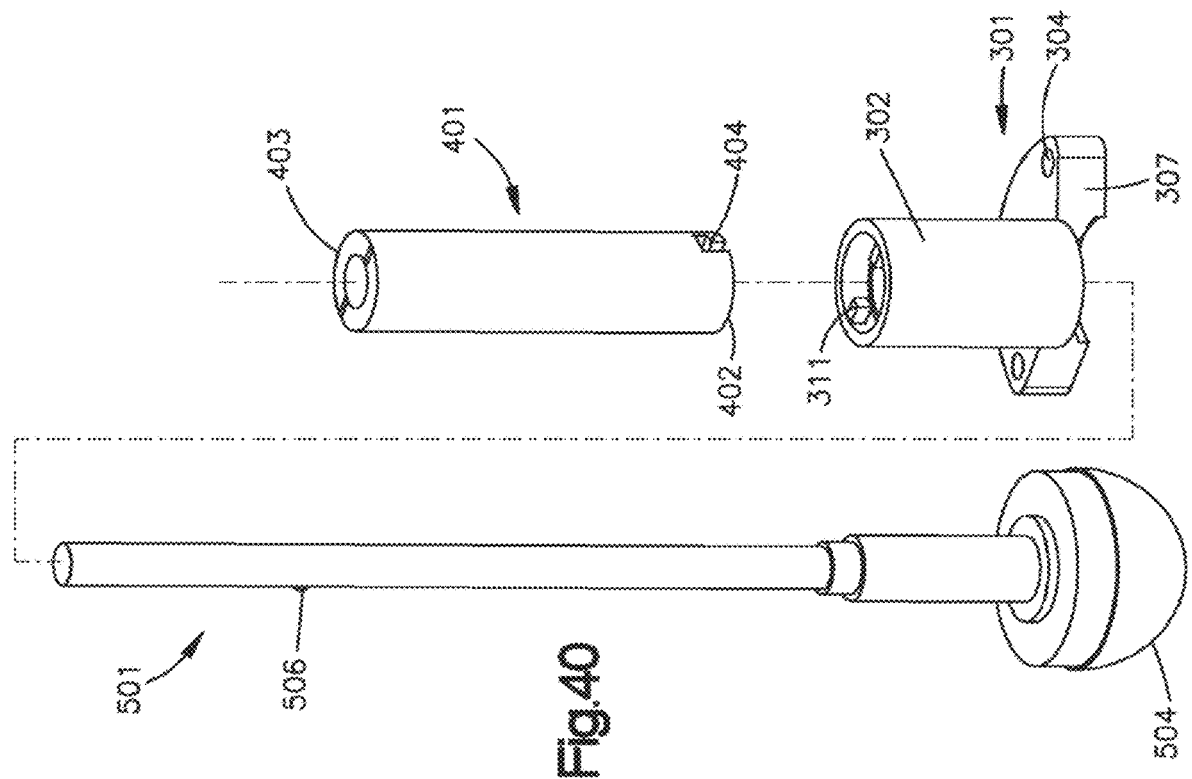
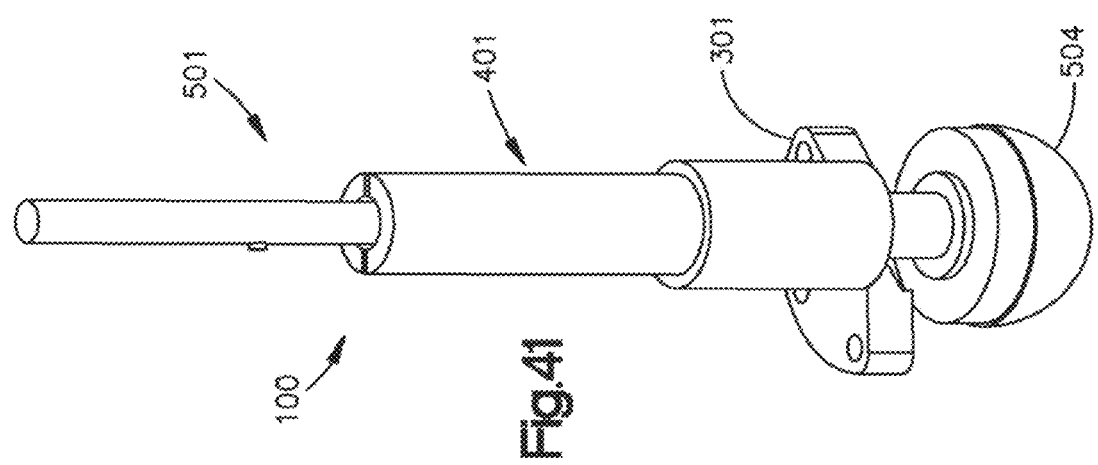

METHODS AND DEVICES FOR POSITIONING A PATIENT-SPECIFIC ACETABULUM REAMING AND CUP POSITIONING GUIDE

CROSS-REFERENCE TO RELATED APPLICATIONS

This application is a continuation of U.S. application Ser. No. 15/630,274, filed Jun. 22, 2017; which claims the benefit of a continuation of U.S. application Ser. No. 14/321,925, filed Jul. 2, 2014, now U.S. Pat. No. 9,693,785; which claims the benefit of U.S. Provisional Application No. 61/841,964, filed Jul. 2, 2013, the entire contents of which are incorporated herein by reference.

BACKGROUND OF THE INVENTION

Statement Regarding Federally Sponsored Research or Development

This application is not the subject of any federally sponsored research or development.

The Names of the Parties to a Joint Research Agreement

There have been no joint research agreements entered into with any third parties.

Field of the Invention

The embodiments of the present invention relate generally to a device for a patient-specific acetabular reaming and cup positioning guide. In particular, the embodiments of the present invention are directed to a device that includes a patient-specific guide and template for use in total hip arthroplasty surgeries.

Background

Total Hip Arthroplasty ("THA") is a complex orthopedic operation in which surgeons replace a diseased hip joint with implants. THA is commonly performed to relieve joint pain and improve quality of life. Approximately 200,000 THA surgeries are performed each year in the United States, and the number is likely to reach 570,000 by the year 2030. The current costs of THA surgery is approximately $25,000.

A rising percentage of patient research information about THA surgical technologies and surgeons before making the final decision regarding surgery. As a result, the THA market is driven by well-educated patients and their demand for technological advances, which further drives the need for improved acetabular reaming and positioning guides, and devices directed to the same.

As shown in FIGS. 11-13, which are explained in further detail below, the acetabulum is the socket of the hip bone, into which the head of the femur fits. It is essentially a concave cavity that receives the femoral head, where the femoral head is able to move (i.e., the ball shaped head on the top of the femur is able to rotate around in the concave cavity forming a "ball and socket" joint). Reaming is a process in which surgeons use a reamer to remove diseased bone and cartilage. Reaming also determines the correct size and position of the socket in preparation for the placement of acetabular component.

Properly reaming the acetabular socket and placing the implant in a suitable position and orientation is critical for the success of a THA surgery. Inaccurate implant placement can contribute to various complications such as bearing surface wear, implant dislocation, limb length discrepancy, component impingement, osteolysis, implant loosening, and premature or early failure. These complications can lead to hospital readmission and revision surgery, and can result in a poor clinical outcome and significantly increase healthcare costs.

Acetabular socket reaming and implant placement is a complicated and time consuming procedure. In currently available surgical techniques, the dominant method is the traditional freehand method that involves making a 4 to 8 inch incision on the side of the hip. The clinical outcome relies heavily on the surgeon's experience and onsite execution. Because the socket is deep within the incision and surrounded by muscles, fat, and other soft tissues, it is difficult for even well-experienced and high-volume surgeons to consistently attain correct acetabular component orientation and position, especially for high body mass index ("BMI") patients. Minimally invasive surgery ("MIS") allows the surgeon to perform the THA surgery through a smaller incision (approximately 3 to 6 inch). MIS incision candidates are typically thinner, younger, healthier, and more motivated to have a quick recovery and shorter hospital stay. However, MIS has not shown any better long-term clinical outcomes than traditional THA surgery. Its learning curve is long and it is easier for new surgeons to make mistakes due to limited vision of the surgical site.

Image-guided navigation surgery uses computer surgical planning to determine the implant size and alignment preoperatively. The surgery is executed with the help of intraoperative implant registration instruments. The surgery can achieve high accuracy and consistency, but the application has been jeopardized by high instrument costs, long operative time, and a steep learning curve.

Use of patient-specific surgical guides/templates is a relatively new technique and has been used in the installation of dental implants. It is usually designed in a computer surgical planning procedure based on a patient's bone geometry (three-dimensional reconstruction of CT or MRI images) and then manufactured using medical grade plastic materials. The template can be fixed onto a unique area of the bone and includes a structure that can guide surgical tools through certain locations and directions to remove bone with precision and place implants with proper orientation consistently. The computer surgical plan is usually approved by a surgeon and if properly designed and executed, the guide will help the surgeon replicate the plan in patients to achieve optimal implant position and orientation. In recent years, surgical guides are becoming more common in orthopedic surgeries. An example of a custom-fit surgical guide for total knee arthroplasty ("TKA") can be found in U.S. Patent Application Publication No. 2010/0049195 to Park et al., entitled "Arthroplasty System and Related Methods." Due to successful clinical outcomes, similar surgical guides have been used by more and more surgeons to replace the costly navigation guided TKA surgery and reduce operative time.

In the case of acetabular reaming and positioning guides current techniques have various limitations. For example in the guide described in U.S. Patent Application Publication No. US 2012/0041445, the cylinder may be too big and can impinge with the femur even when the femoral head/neck is removed, resulting in the guide not sitting in the intended position to achieve accurate reaming. Another issue is that the three legs are too long. The surgeon will need to remove significant amounts of the soft tissue around the acetabular rim to allow the legs to sit at the right locations. If this soft tissue is not removed, inaccurate location of the three legs will change the orientation and location of the reamer and eventually influence the accuracy of the implant placement. The same issue exists in the guide disclosed in International Patent Application Publication No. WO 2012/010366, wherein the three legs require large soft tissue cuts and may lead to inaccurate reamer orientation and positioning. In addition, the reamer and its connected guide part are not designed for easy installation, which is required during the surgery to change reamers and remove bone.

There is currently a need for an improved THA surgical guide in the medical device market. Specifically, there exists a need for a patient-specific guide/template for both surgeons and patients of THA. The embodiments of the present invention properly solve the problems of the prior art.

SUMMARY OF THE INVENTION

For the reasons included above, it is therefore an object of embodiments of the present invention to provide a device, system, and method that includes a patient-specific guide and template for use in THA surgeries.

The embodiments of the present invention include a device for use in total hip arthroplasty surgery that includes first, second, third, and fourth guide members. The first guide member includes a substantially semi-circular ring having a top surface and a bottom surface, a plurality of first guide legs protruding vertically downward from the lower surface of the semi-circular ring, the first guide legs including a contact area disposed on the open end of the first guide leg; a plurality of holes disposed on the ring, and a plurality of protrusions extending vertically upward from a top surface of the ring. The second guide member includes an arc having an arc of curvature substantially similar to the semi-circular ring, the arc having a top surface and bottom surface, first and second horizontal brackets connecting ends of the arc and being connected thereto at a termination point, a plurality of second guide legs protruding vertically from either the lower surface of the arc, first or second horizontal brackets; and means for connecting the second guide member to the first guide member. The third guide member includes a cylindrical first tube; and a horizontal plate connected to the tube having a top surface and a lower surface, where the lower surface includes the engagement surface for engagement with the first guide member; and a plurality of holes disposed on the plate, where posts protruding from the top surface of the semi-circular ring are capable of entering the plurality of holes disposed on the plate to engage the first guide member with the third guide member. A fourth guide member includes a cylindrical second tube capable of being connected to the first tube, where the outside diameter of the second tube is less than the inside diameter of the first tube to allow engagement; and means for engaging the second tube to the first tube.

Yet another embodiment of the present invention is directed to a device for use in total hip arthroplasty surgery including a first guide member having a substantially semi-circular ring having a top surface and a bottom surface, a plurality of first guide legs protruding vertically downward from the lower surface of the semi-circular ring, the first guide legs including a contact area disposed on the open end of the first guide leg; a plurality of holes disposed on the ring, a plurality of protrusions extending vertically upward from a top surface of the ring. The device also includes a third guide member having a cylindrical first tube; and a horizontal plate connected to the cylindrical first tube having a top surface and a lower surface, where the lower surface includes the engagement surface for engagement with the first guide member; and a plurality of holes disposed on the plate, wherein posts protruding from the top surface of the semi-circular ring are capable of entering the plurality of holes disposed on the plate to engage the first guide member with the third guide member. The device also includes a fourth guide member including a cylindrical second tube capable of being connected to the first tube, wherein the outside diameter of the second tube is less than the inside diameter of the first tube to allow engagement; and means for engaging the second tube to the first tube.

The embodiments of the present invention are further directed to a device for use in total hip arthroplasty surgery that includes a first guide member having a substantially semi-circular ring having a top surface and a bottom surface, a plurality of first guide legs protruding vertically downward from the lower surface of the semi-circular ring, the first guide legs including a contact area disposed on the open end of the first guide leg; a plurality of holes disposed on the ring, a plurality of protrusions extending vertically upward from a top surface of the ring. The device also includes a third guide member having a cylindrical first tube; and a horizontal plate connected to the cylindrical first tube having a top surface and a lower surface, wherein the lower surface includes the engagement surface for engagement with the first guide member; and a plurality of holes disposed on the plate, wherein posts protruding from the top surface of the semi-circular ring are capable of entering the plurality of holes disposed on the plate to engage the first guide member with the third guide member. The device also includes a fourth guide member having a cylindrical second tube capable of being connected to the first tube, wherein the outside diameter of the second tube is less than the inside diameter of the first tube to allow engagement; and means for engaging the second tube to the first tube. The plurality of first guide legs have the same or different lengths depending on the patient's specific needs, and the contact areas include flat, concave, and convex shapes to fit a patient's hip joint.

BRIEF DESCRIPTION OF THE DRAWINGS

Preferred features of the embodiments of the present invention are disclosed in the accompanying drawings, wherein similar reference characters denote similar elements throughout the several views, and wherein:

FIG. 32 is a front/top perspective view of a third guide according to an embodiment of the present invention;

FIG. 33 is a top/rear perspective view of a third guide according to an embodiment of the present invention;

FIG. 34 is a side perspective view of a third guide according to an embodiment of the present invention;

FIG. 40 is a perspective view of a reamer, third guide and fourth guide according to an embodiment of the present invention including a dashed line that shows how they are connected together;

FIG. 41 is a perspective view of an assembled reamer, third guide and fourth guide according to an embodiment of the present invention;

DETAILED DESCRIPTION

Figure 1:
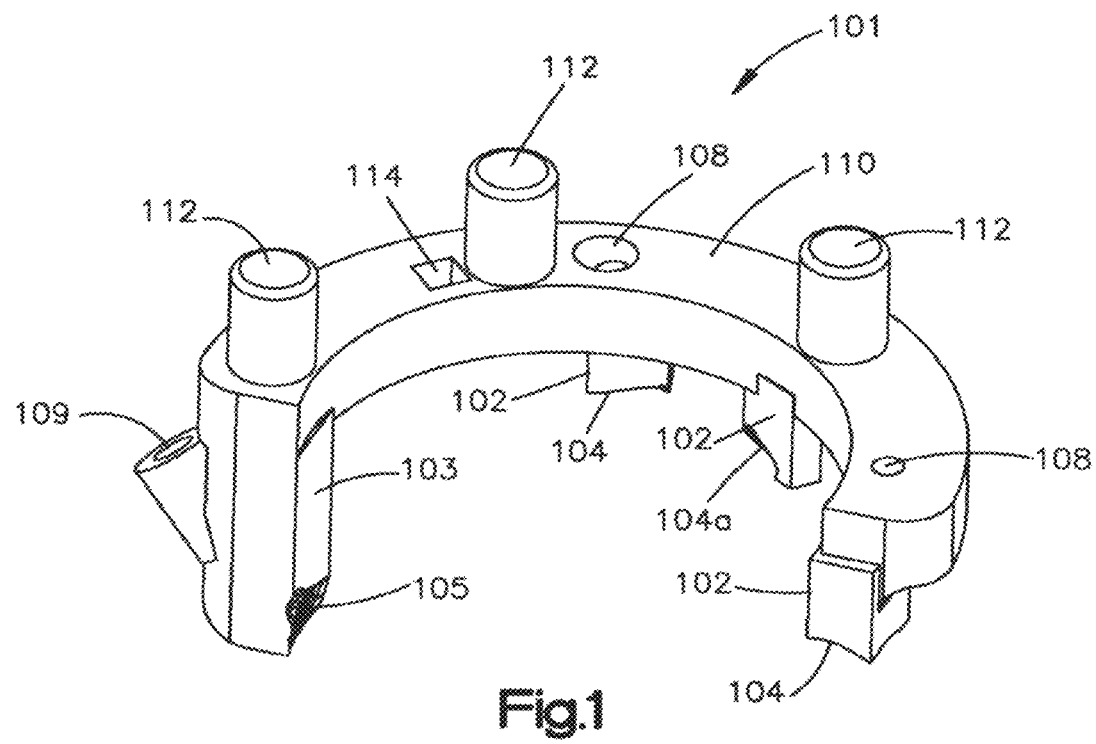
FIG. 1 is a top/front perspective view of a first guide according to an embodiment of the present invention.

The embodiments of the present invention will now be described more fully hereinafter with reference to the accompanying drawings, in which preferred embodiments of the invention are shown. This invention may, however, be embodied in many different forms and should not be construed as limited to the illustrated embodiments set forth herein. Rather, these illustrated embodiments are provided so that this disclosure will be thorough and complete and will convey the scope of the invention to those skilled in the art.

In the following description, like reference characters designate like or corresponding parts throughout the figures. Additionally, in the following description, it is understood that terms such as "top," "bottom," "side," "front," "back," "inner," "outer," and the like, are words of convenience and are not to be construed as limiting terms.

Use of a patient-specific surgical guide/template is a relatively new technique. It is usually designed in a computer surgical planning procedure based on a patient's bone geometry (a three-dimensional reconstruction of CT or MRI images). When the computer surgical plan is approved by a surgeon, the template can be manufactured using plastic materials or the like. The surgical guide/template may be manufactured, for example, through the use of three-dimensional (3D) printing technology, stereolithography, or the like. The template can be fixed onto a unique area of the bone and includes a structure that can guide a reamer to remove bone with certain orientation and depth. The template can also help to place the permanent acetabular component.

Figure 11A:
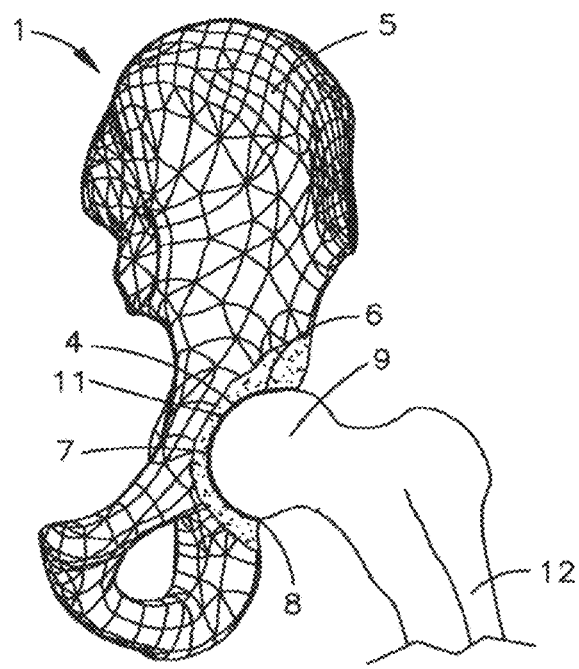
FIG. 11A is a drawing depicting a healthy acetabulum and femur.
Figure 11B:
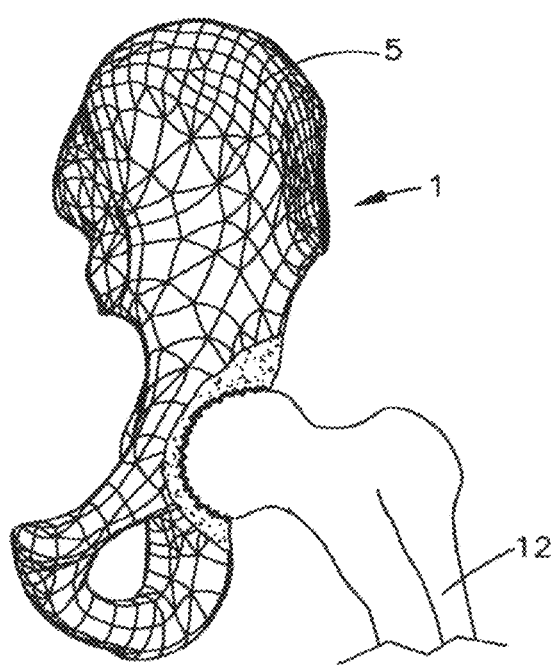
FIG. 11B is a drawing depicting an acetabulum and femur with osteoarthritis.
Figure 12:
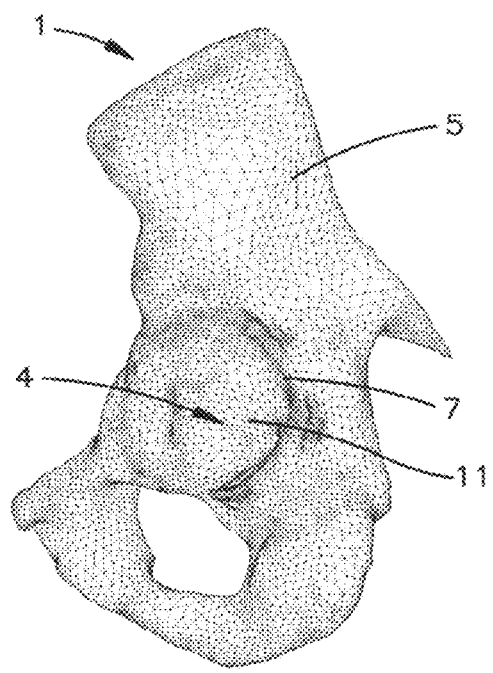
FIG. 12 is a drawing depicting an acetabulum.
Figure 13:
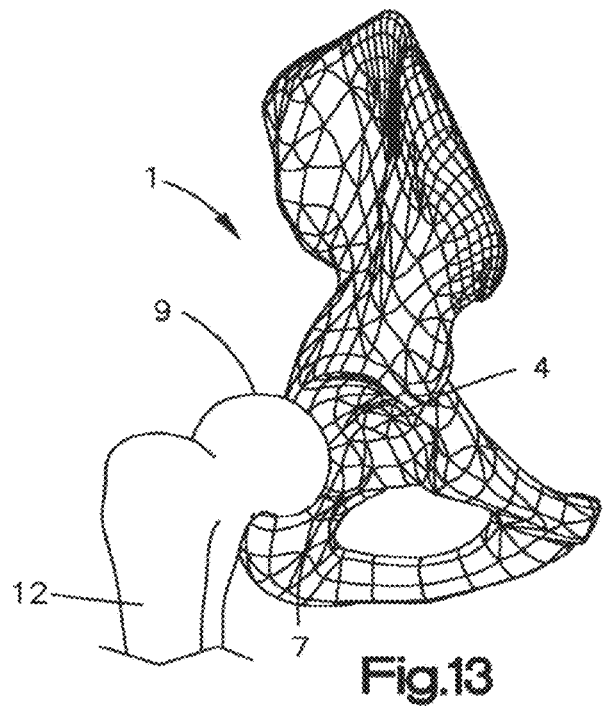
FIG. 13 is a drawing depicting an acetabulum and femur.
Figure 14B:
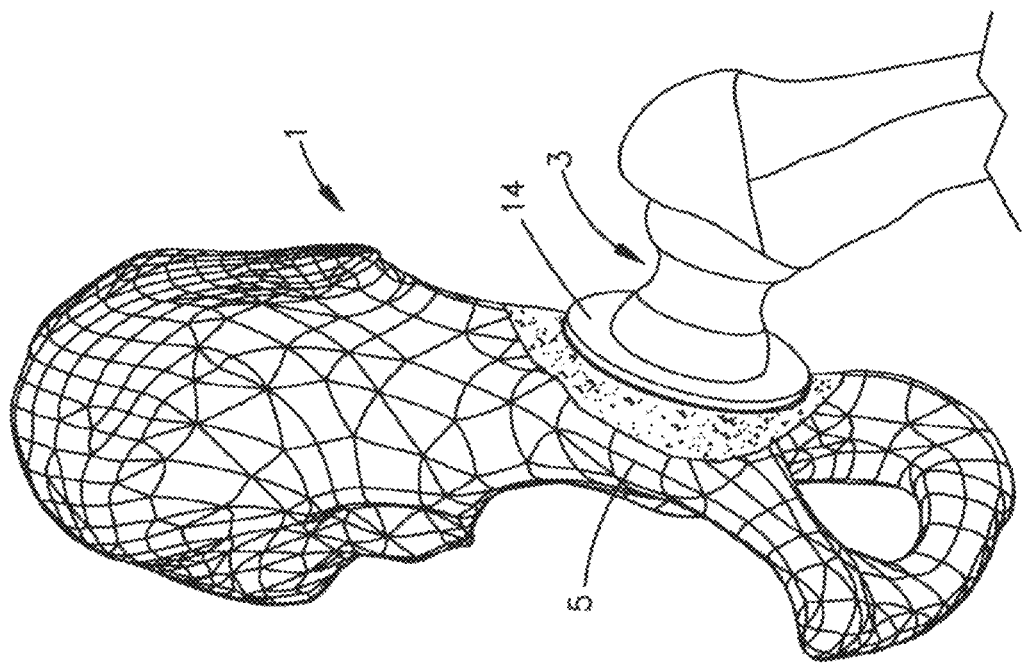
FIG. 14B is a drawing depicting a hip joint after THA surgery
Figure 14A:
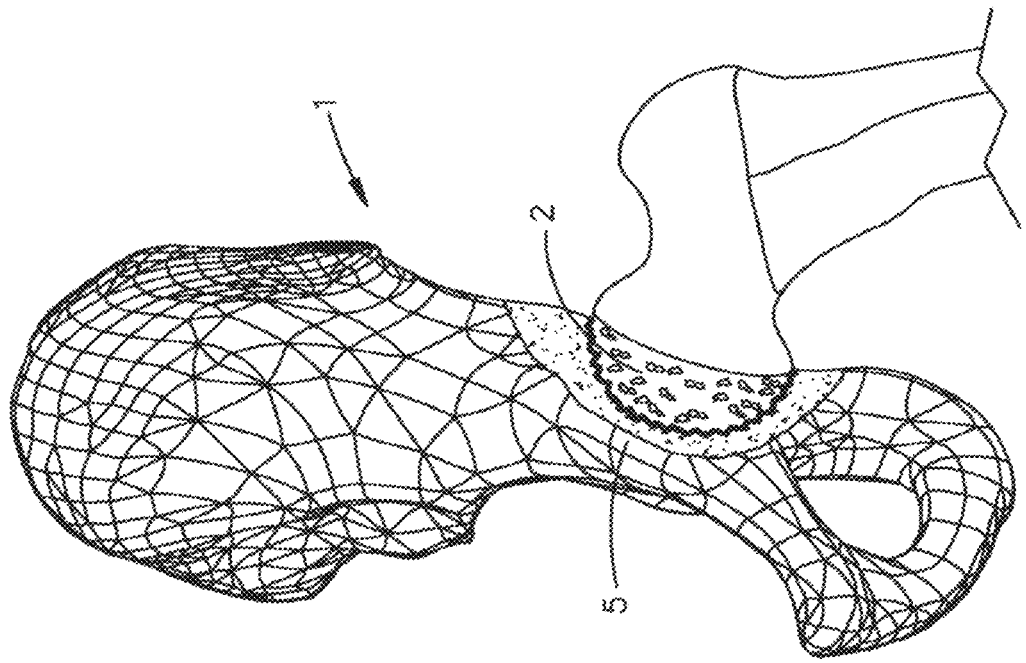
FIG. 14A is a drawing depicting a hip joint with osteoarthritis.
Figure 15:
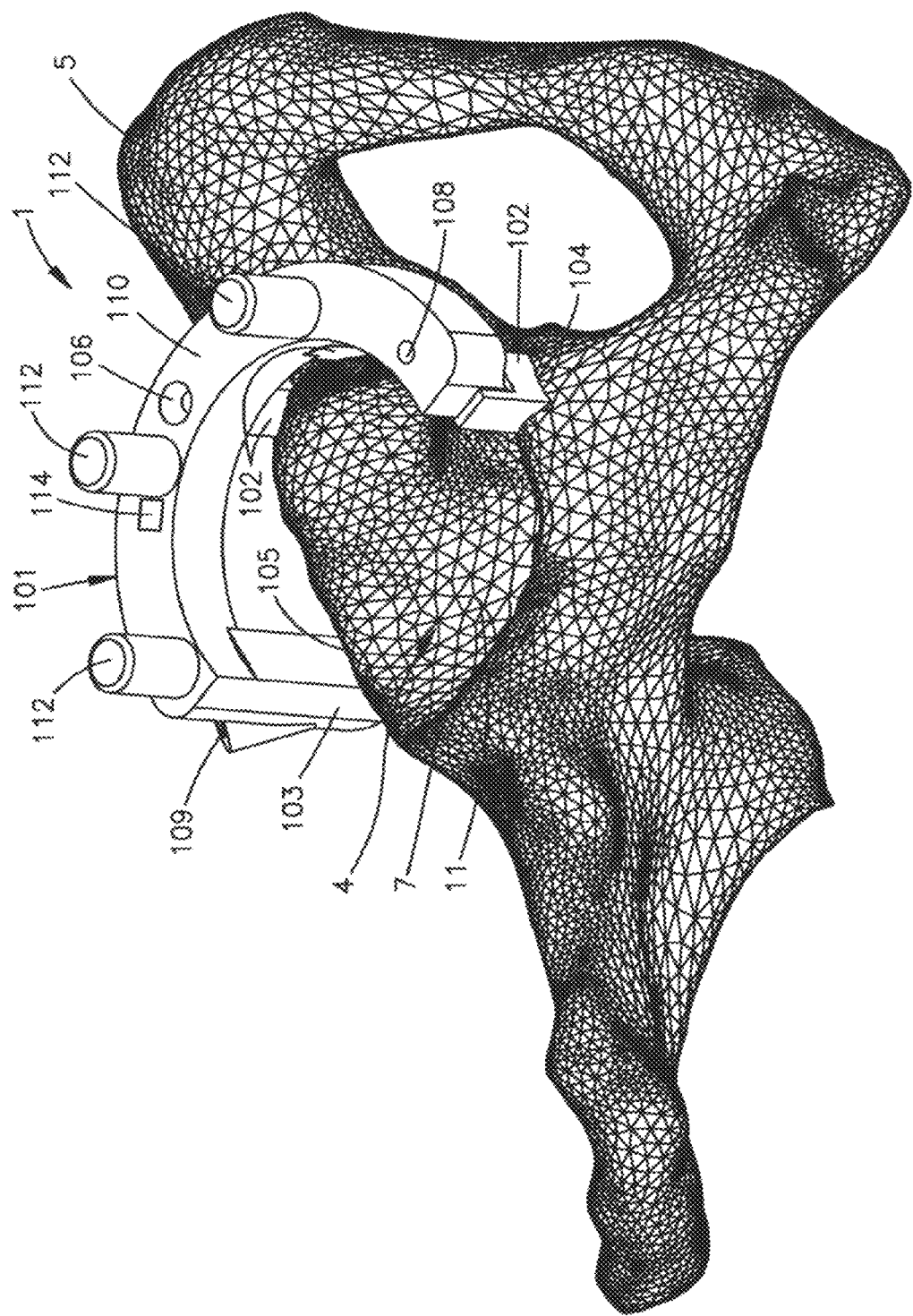
FIG. 15 is a top/side perspective view of a first guide engaged with a hip joint according to an embodiment of the present invention.
Figure 16:
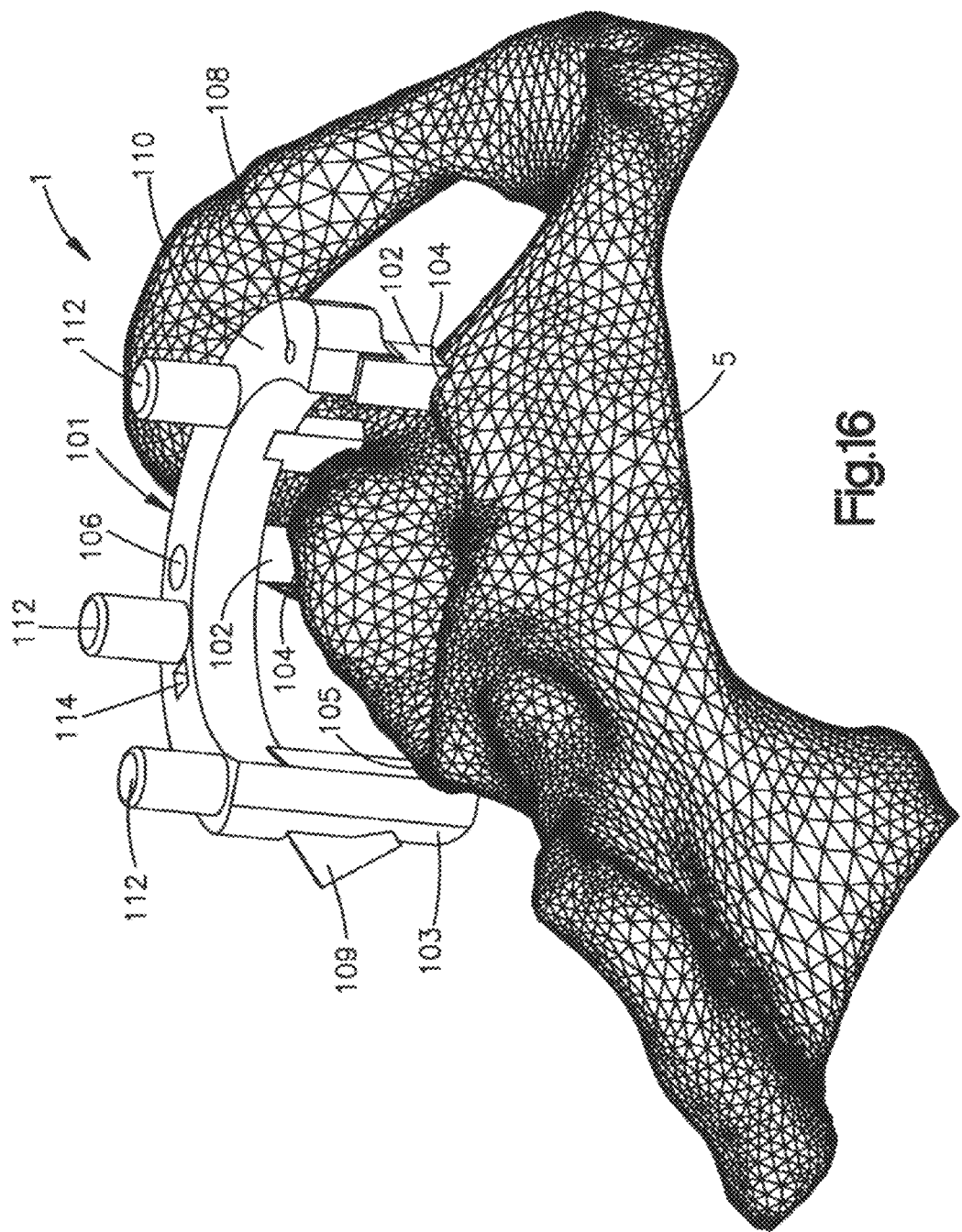
FIG. 16 is a front perspective view of a first guide engaged with a hip joint according to an embodiment of the present invention.
Figure 17:
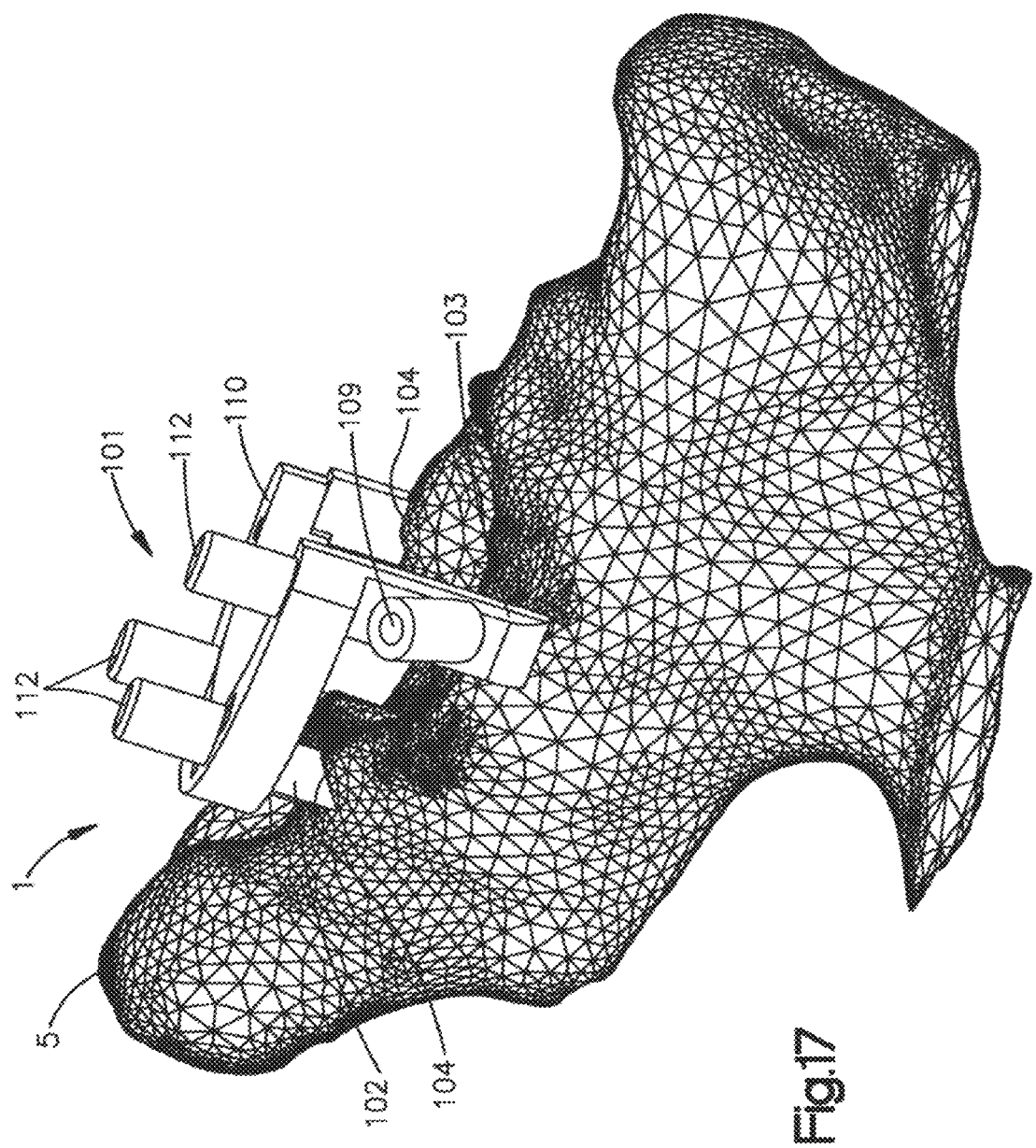
FIG. 17 is a side perspective view of a first guide engaged with a hip joint according to an embodiment of the present invention.
Figure 18:
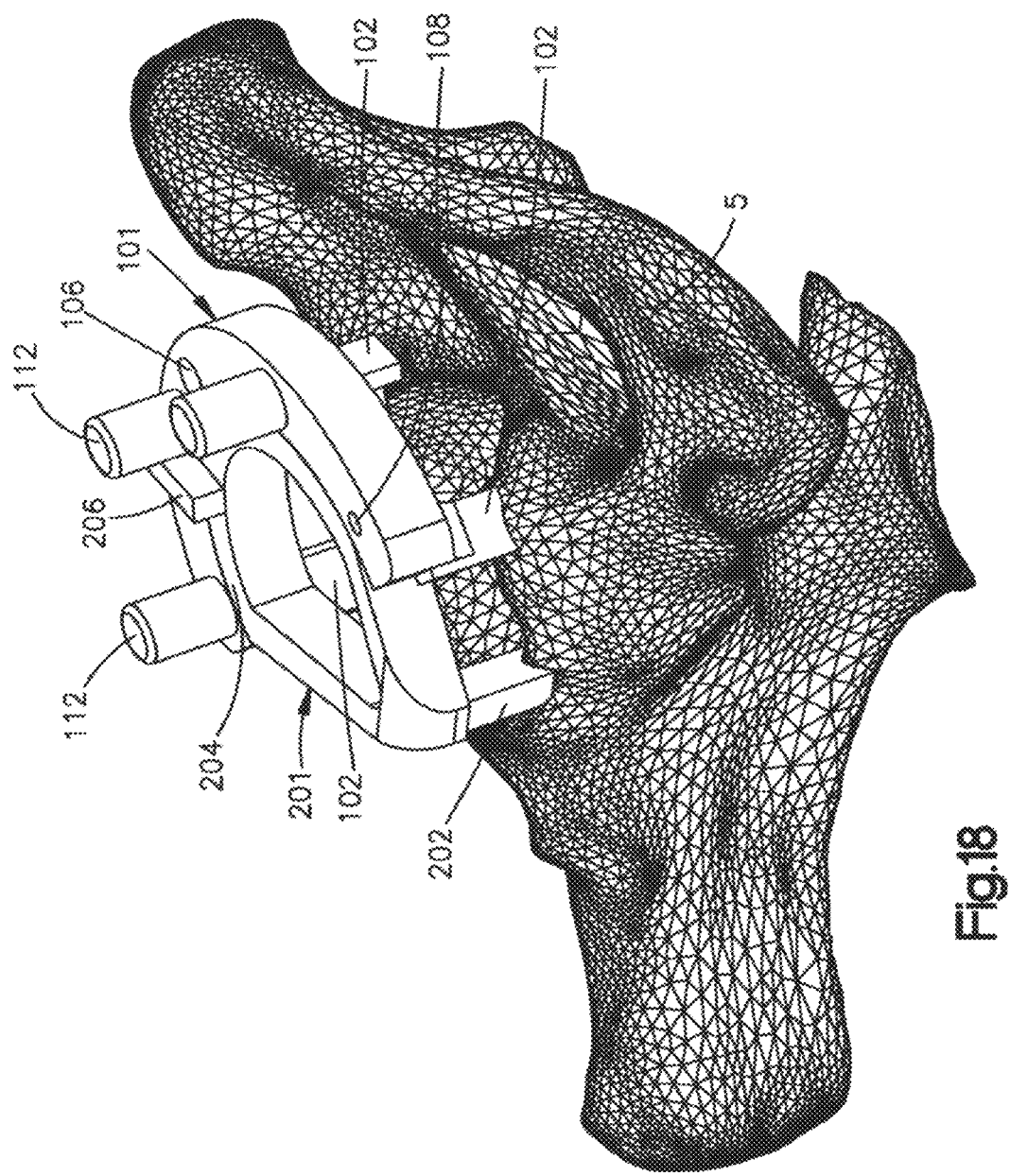
FIG. 18 is a top/side perspective view of a first guide and a second guide engaged with a hip joint according to an embodiment of the present invention.
Figure 19:
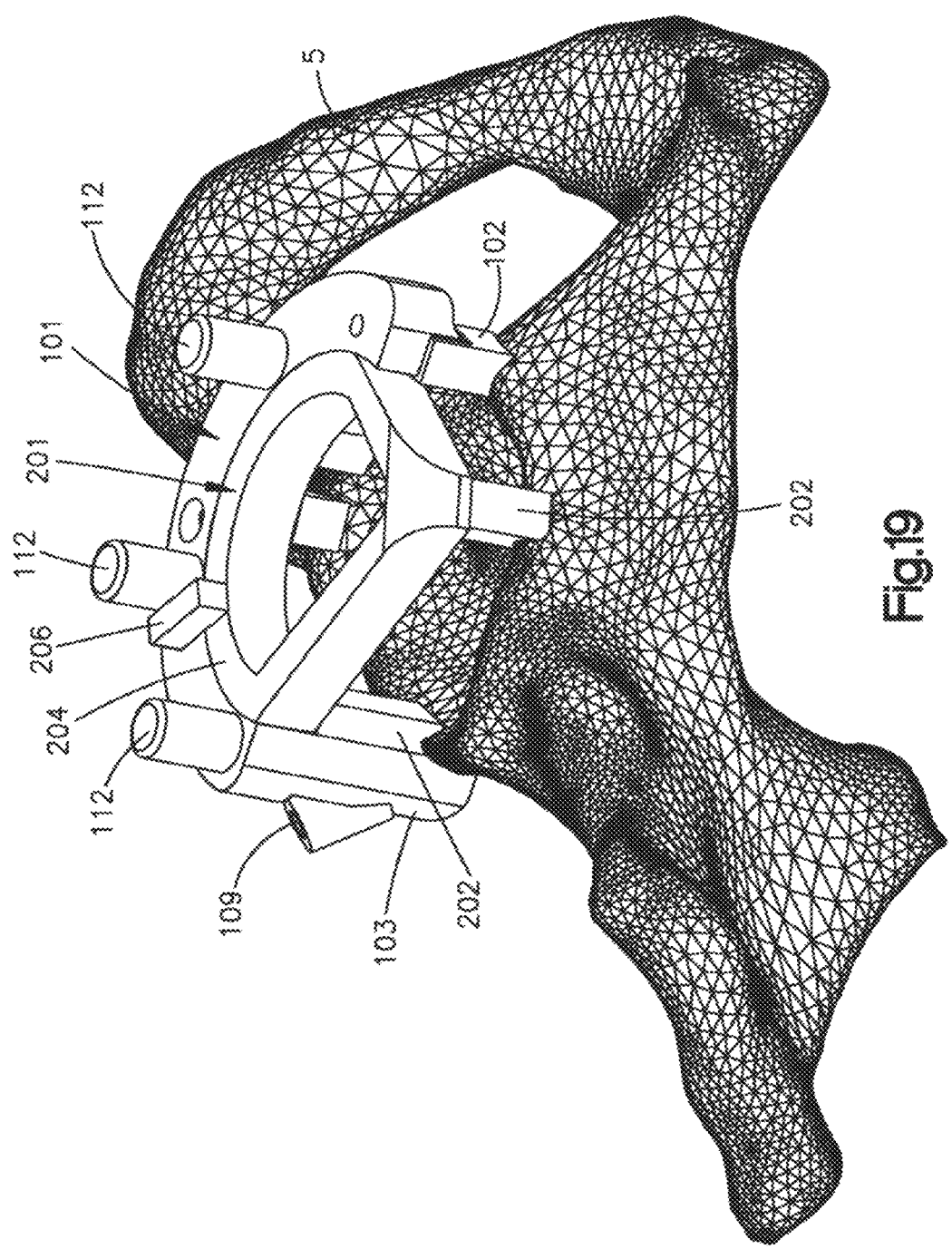
FIG. 19 is a front perspective view of a first guide and a second guide engaged with a hip joint according to an embodiment of the present invention.
Figure 20:
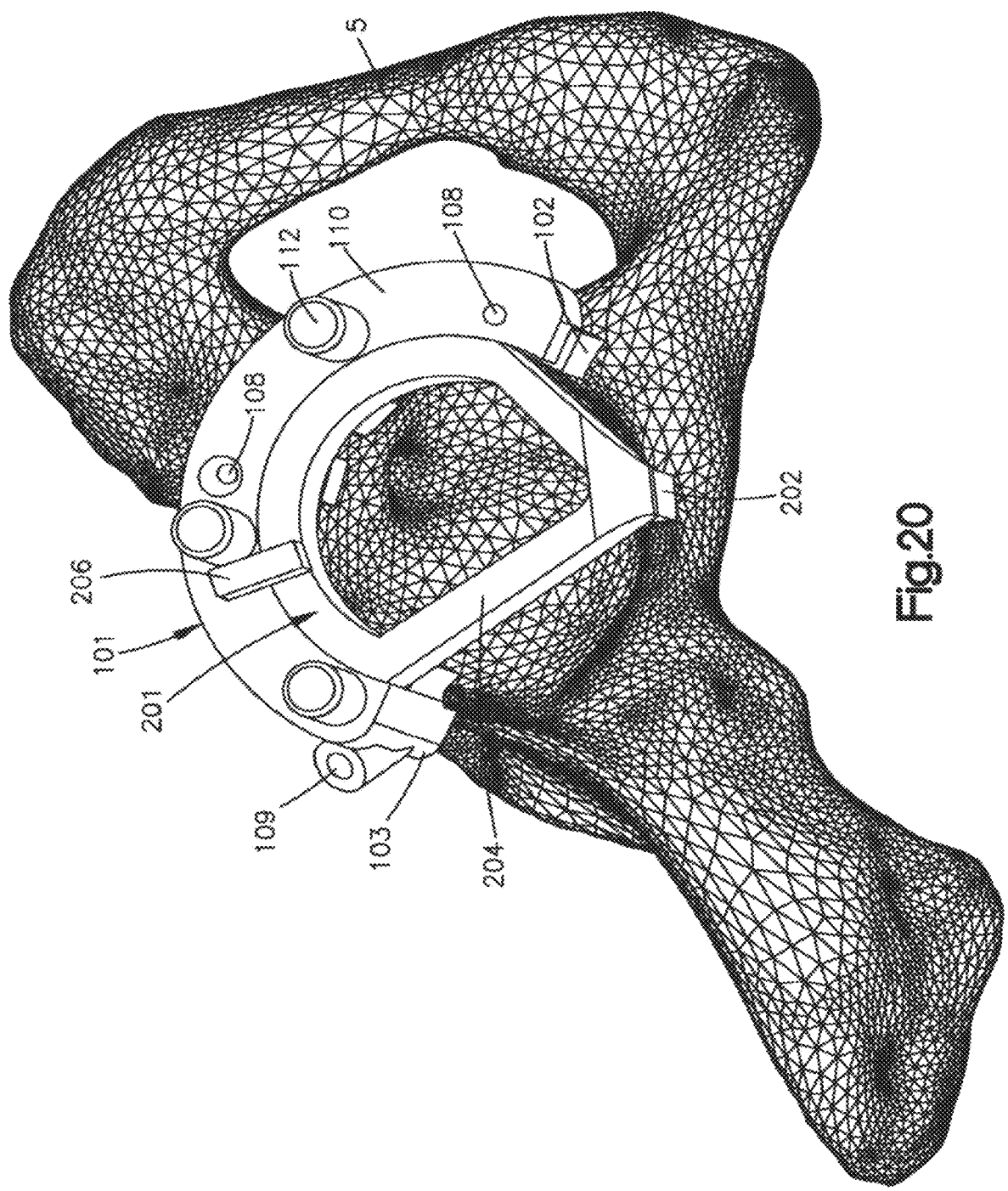
FIG. 20 is a top perspective view of a first guide and a second guide engaged with a hip joint according to an embodiment of the present invention.
Figure 21:
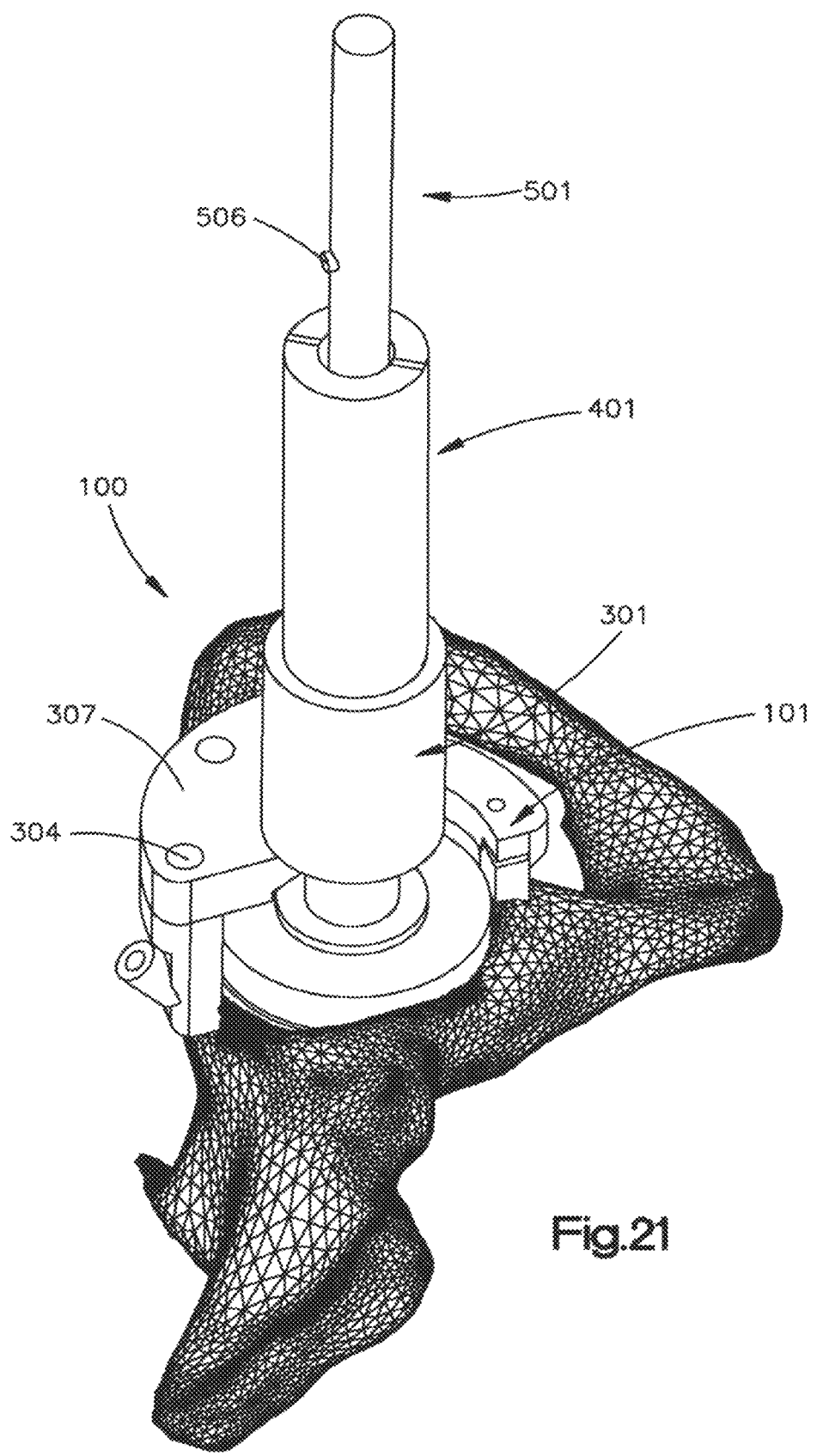
FIG. 21 is a top/side perspective view of a first guide, third guide and fourth guide with a reamer engaged with an acetabulum according to an embodiment of the present invention.
Figure 22:
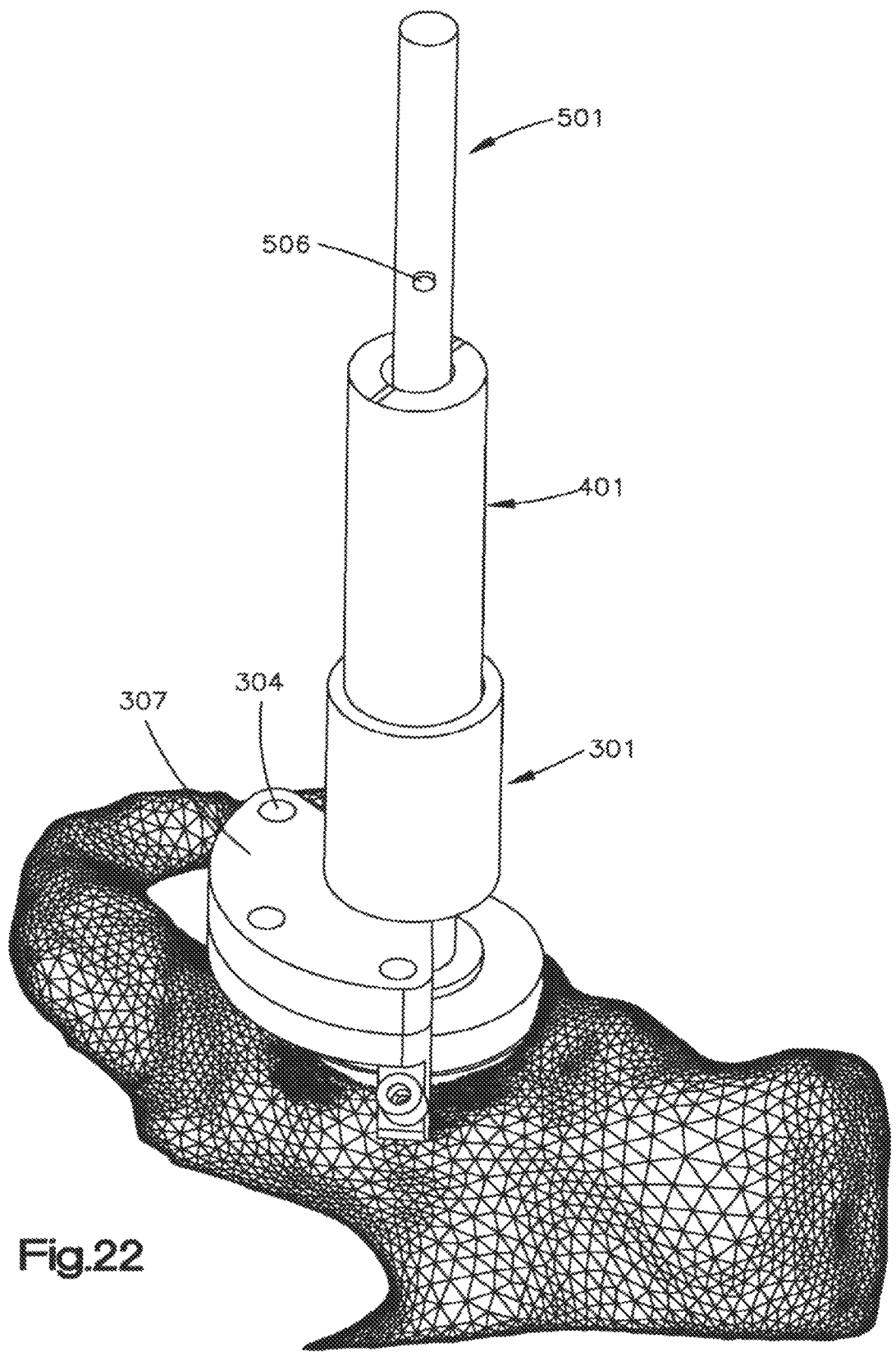
FIG. 22 is a top/side perspective view of a first guide, third guide and fourth guide with a reamer engaged with an acetabulum according to an embodiment of the present invention.
Figure 23:
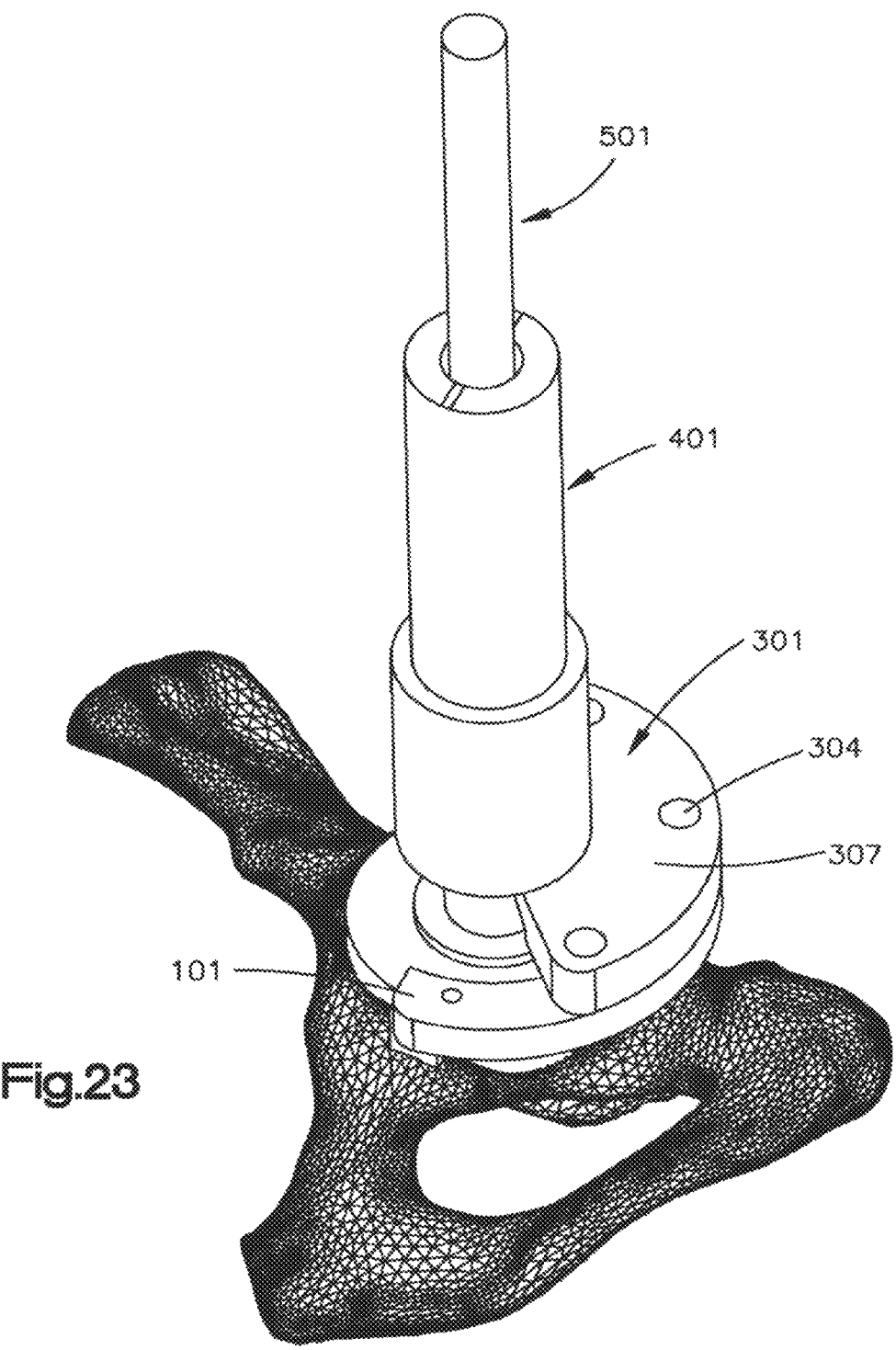
FIG. 23 is a top perspective view of a first guide, third guide and fourth guide with a reamer engaged with an acetabulum according to an embodiment of the present invention.

FIGS. 4, 11A, 11B, 12, 13, 14A, and 14B show a hip joint 1. Specifically, FIGS. 14A and 14B depict a rendition of a hip joint 1 with osteoarthritis 2 and a rendition of a hip joint 1 with a THA implant 3, respectively. In addition, FIG. 11A depicts a healthy hip joint 1, where the acetabulum 4 is the socket shaped concave structure in the pelvic bone 5 that is lined with healthy cartilage 6. The acetabulum 4 includes an acetabular rim 7, an acetabular notch 8, and an acetabular socket 11. The femoral head 9 of the femur 12 (thigh bone) acts as a ball that fits into the acetabular socket 11. These components form the main structure of the hip joint 1.

As described above, reaming is a process used by surgeons to remove arthritic bone from the acetabulum 4, where a reamer 501 is used to remove diseased bone and cartilage. Reaming also aids in providing the correct size of the new socket for an implant (acetabular component) 14.

The embodiments of the present invention were developed through computer planning and simulation of various surgeries such as THA, total knee arthroplasty, trauma surgeries, and craniofacial surgeries. The embodiments of the present invention include a patient-specific acetabular reaming and guide device 100, methods of using the same, and a system that includes the device 100 in order to perform a THA surgery.

Specifically, the embodiments of the present invention include an optimal surgical plan (implant selection and placement) based on a patient's specific anatomy before the actual surgery. Furthermore, the embodiments of the present invention include a patient-specific surgical guide system that improves the accuracy of acetabular reaming and implant placement in THA surgery, reducing healthcare costs, and improving clinical outcomes.

The system of the preferred embodiment of the present invention includes creating a three-dimensional (3D) computer model (or series of computer models) of the patient's pelvis 5 and femur 12 using CT or MRI scans of the patient. The system further includes a computer-based surgery simulation that is conducted to determine an optimal surgical plan, which will include the size and placement of the acetabular cup 14 and femoral stem.

FIGS. 1-10 will now be described.

Figure 2:
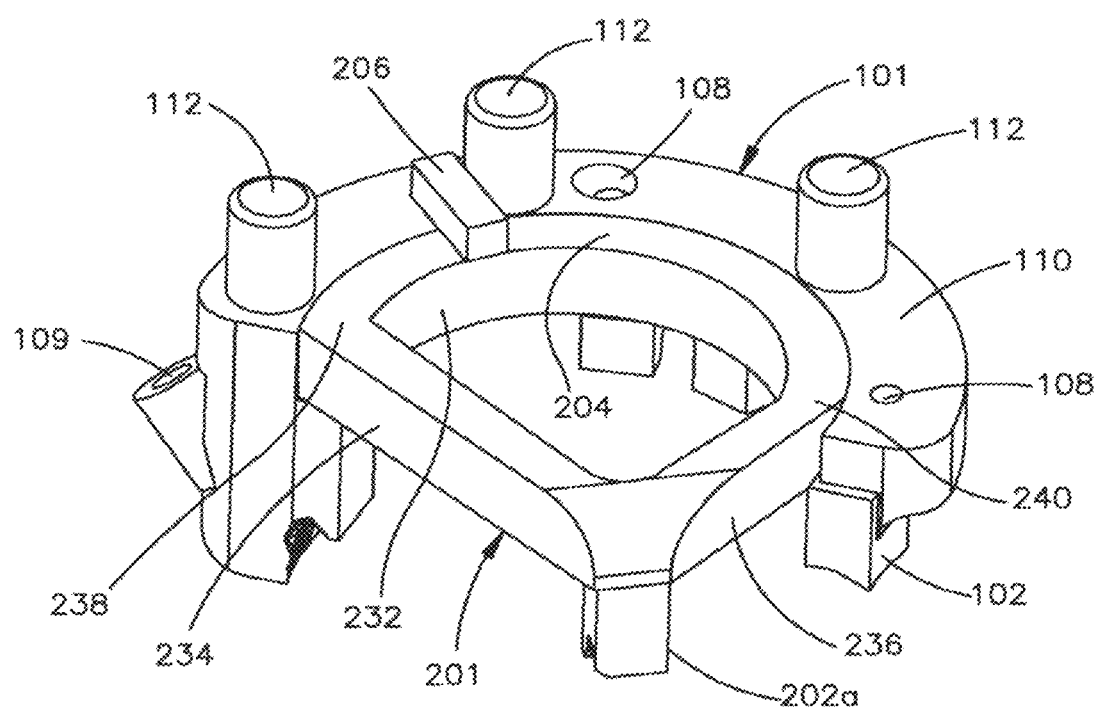
FIG. 2 is a top/front perspective view of a first guide and a second guide according to an embodiment of the present invention.

As shown in FIGS. 1 and 2, in a preferred embodiment of the present invention, the first guide 101 and the second guide 201 connect with one another, where the second guide 201 includes a connecting member 206 having a preferred rectangular shape having a male protrusion (not shown) at a free end that fits into an alignment hole 114 in the first guide 101, which may be in the form of a square hole as shown in FIG. 1. The "means for connecting" as used in the claims includes connecting member 206 and equivalents as appreciated by a person of ordinary skill in the art. First guide 101 generally has the shape of a semi-circular ring with preferably three circular guide posts 112 protruding vertically upwards from the upper surface of the first guide 101 and a plurality of legs 102 protruding vertically downward from the lower surface of the first guide 101. The first guide includes openings 108 for securing members such as screws to secure the first guide to a patient's hip joint; where angular securement is desired, a side of the ring may include a cylindrically shaped member having an opening 109 for a securing means such as a screw to secure the first guide 101 to the patient's hip.

Figure 3:
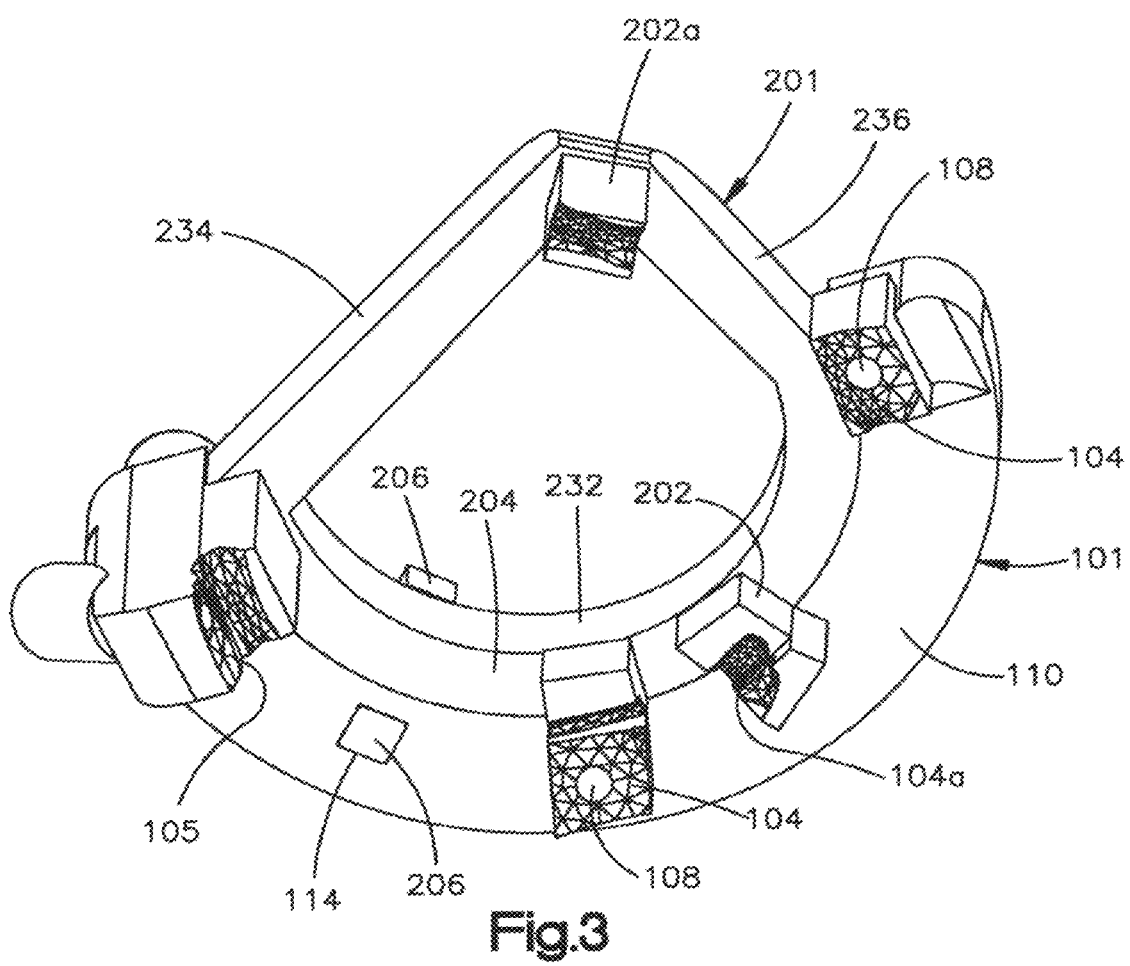
FIG. 3 is a bottom view of a first guide and a second guide according to an embodiment of the present invention.

As depicted in FIGS. 1-3, in a preferred embodiment of the present invention, the first guide 101 includes a plurality of first guide legs 102 extending vertically downward from the lower surface of the first guide 101. The second guide 201 includes a plurality of second guide legs 202 that preferably extend vertically downward from the lower surface of the second guide 201. The legs 102, 202 include contact areas 104 (highlighted in FIG. 3) that can contact and maintain the guides 101, 201 at specific areas on the acetabular rim 7. The legs 102, 202 and contact areas 104 uniquely locate the guide device 100 relative to the acetabulum 4. The legs 102, 202 preferably include a rectangular shape but may include certain designs and shapes as required by patient-specific demands based on the condition of the hip joint and amount of required reaming. The contact areas 104 are preferably disposed on the lower surfaces of the legs 102, 202 and can include flat, concave or convex shapes that match a patient's hip joint in order to effect a secure base and fit on the hip joint; as used in the claims, the "open end" of the legs means the end of the leg not attached to the surface of the semi-circular ring or second guide rim 204. In addition, the lengths of the legs 102, 202 may be the same or vary based on the number of legs needed and patient needs. In addition, the location and amount of the legs 102, 202 on the lower surface of the guides 102, 202 may vary based on the patient's needs. The legs 102, 202 shown in the figures are fixed; however, other embodiments of the present invention allow for certain movement in the clockwise or counterclockwise direction to allow a doctor to position the legs on a patient's hip.

One of the goals of the second guide 201 is to provide extra contacts, secure the guide device 100 more accurately, and increase the stability of the guide system. In some embodiments of the present invention, the second guide 201 may not be needed. The second guide 202 includes a preferred shape and design shown in FIG. 2 having an internal second guide rim 204 having an arc 232 and horizontal brackets 234, 236 (shown in FIG. 3) that allows it to fit comfortably inside first guide 101 and secured to same by connection means 206. The termination point 238 of horizontal brackets 234, 236 preferably includes a leg 202a (shown in FIGS. 2 and 3) for further securing the first guide 101 and second guide 202 to the patient's hip. The brackets 234, 236 preferably include a 12 o'clock to 3 o'clock orientation, respectively, having a substantially 90 degree relationship between the legs (the word "substantially" being used as the angular relationship may vary by 5-10 degrees) with the second guide rim 204 preferably connecting the two brackets 234, 236 at the relative ends 238, 240 of the semi-circular ring of the first guide 101 as best shown in FIGS. 2 and 3.

Figure 4:
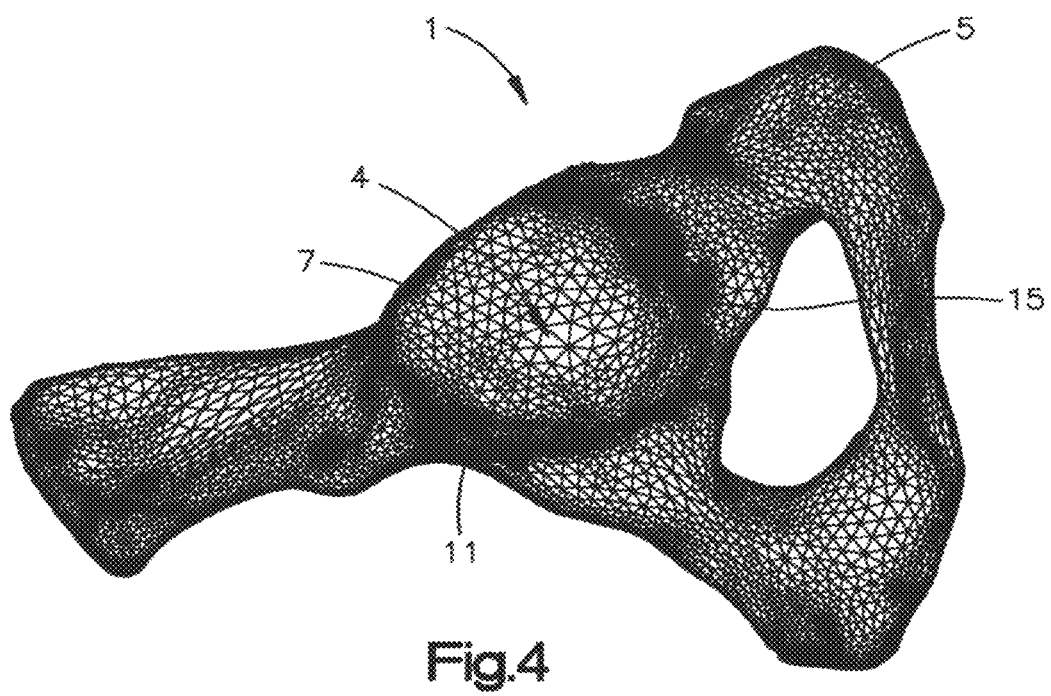
FIG. 4 is a drawing depicting an acetabulum.
Figure 5:
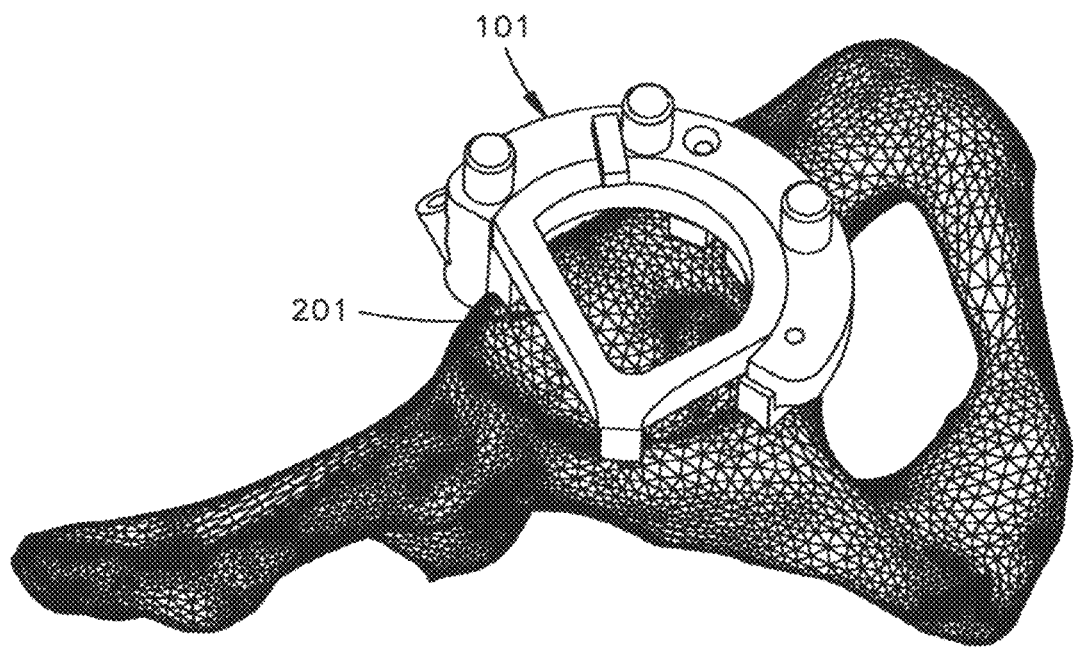
FIG. 5 is a top/front perspective view of a first guide and a second guide engaged with an acetabulum according to an embodiment of the present invention.

As shown in FIGS. 3-5, in a preferred embodiment of the present invention, after the second guide 201 is placed on or inside the first guide 101, the first guide 101 and second guide 201 are placed on the acetabulum 4 by finding the correct place where the contact areas 104 fit properly. Then, in an embodiment of the present invention, screws or other securing means known in the art are inserted through holes 108 or 109 as needed to lock the first guide 101 onto the acetabulum 4. An embodiment of the present invention includes a special contact area 104a that engages with and fits to the acetabular notch 8 thereby preventing rotation of the guide device 100. The engagement of the special contact area 104a and acetabular notch 15 further improves the positioning and stability of the guide device 100.

Figure 6:
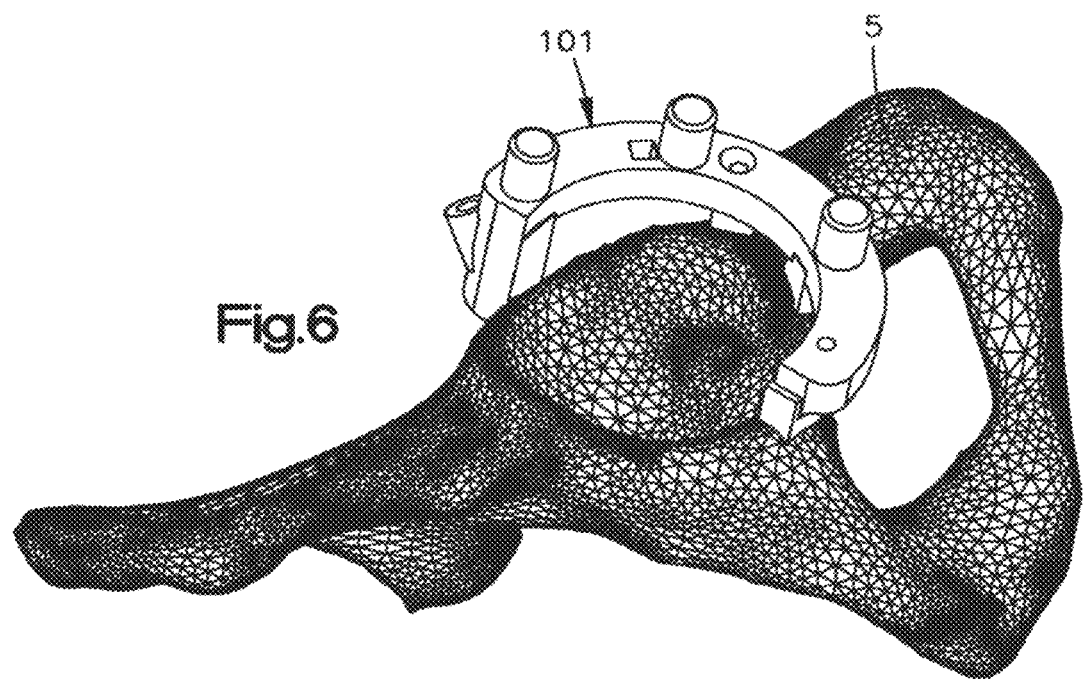
FIG. 6 is a front perspective view of a first guide engaged with an acetabulum according to an embodiment of the present invention.
Figures 7, 7A:
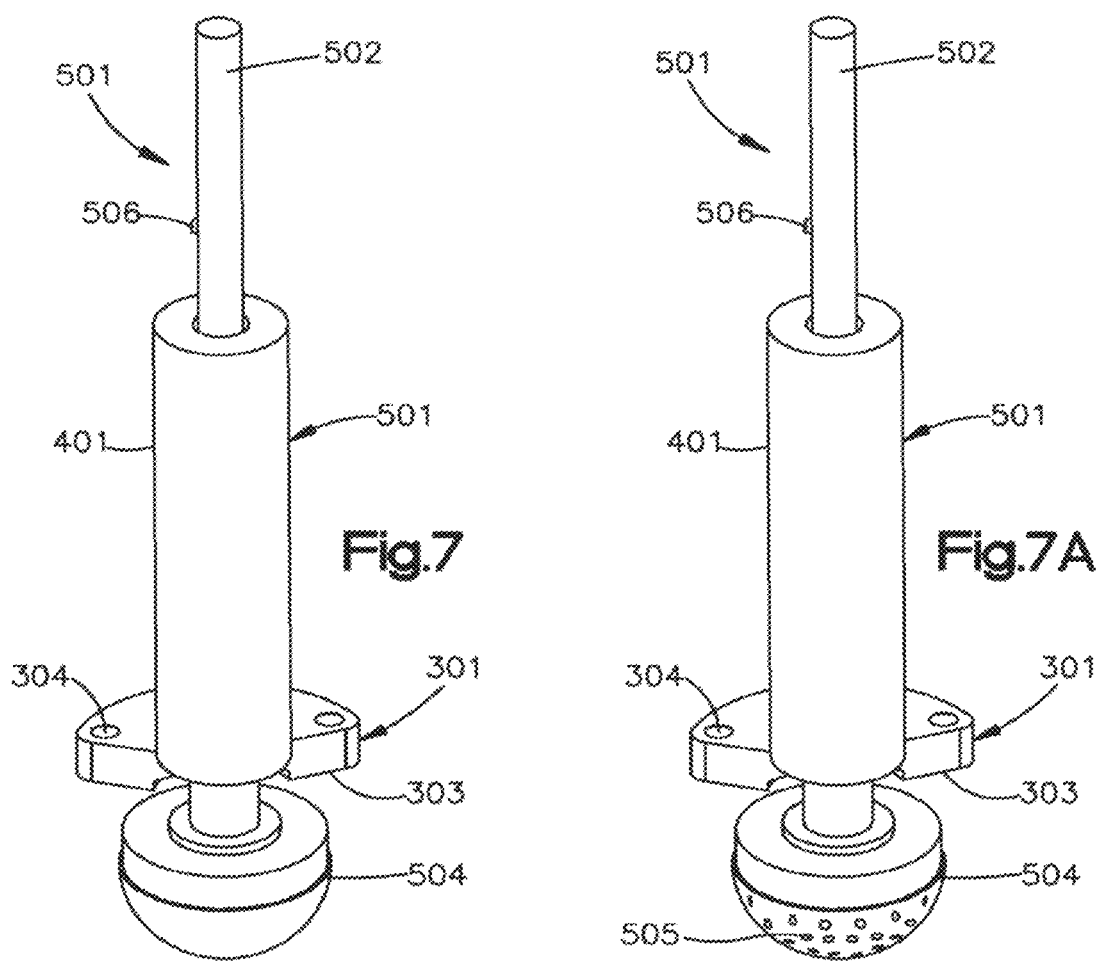
FIG. 7 is a front perspective view of a third guide with a reamer according to an embodiment of the present invention.
FIG. 7A is a front perspective view of a third guide with a reamer according to an embodiment of the present invention where the reamer includes a plurality of holes.
Figure 8:
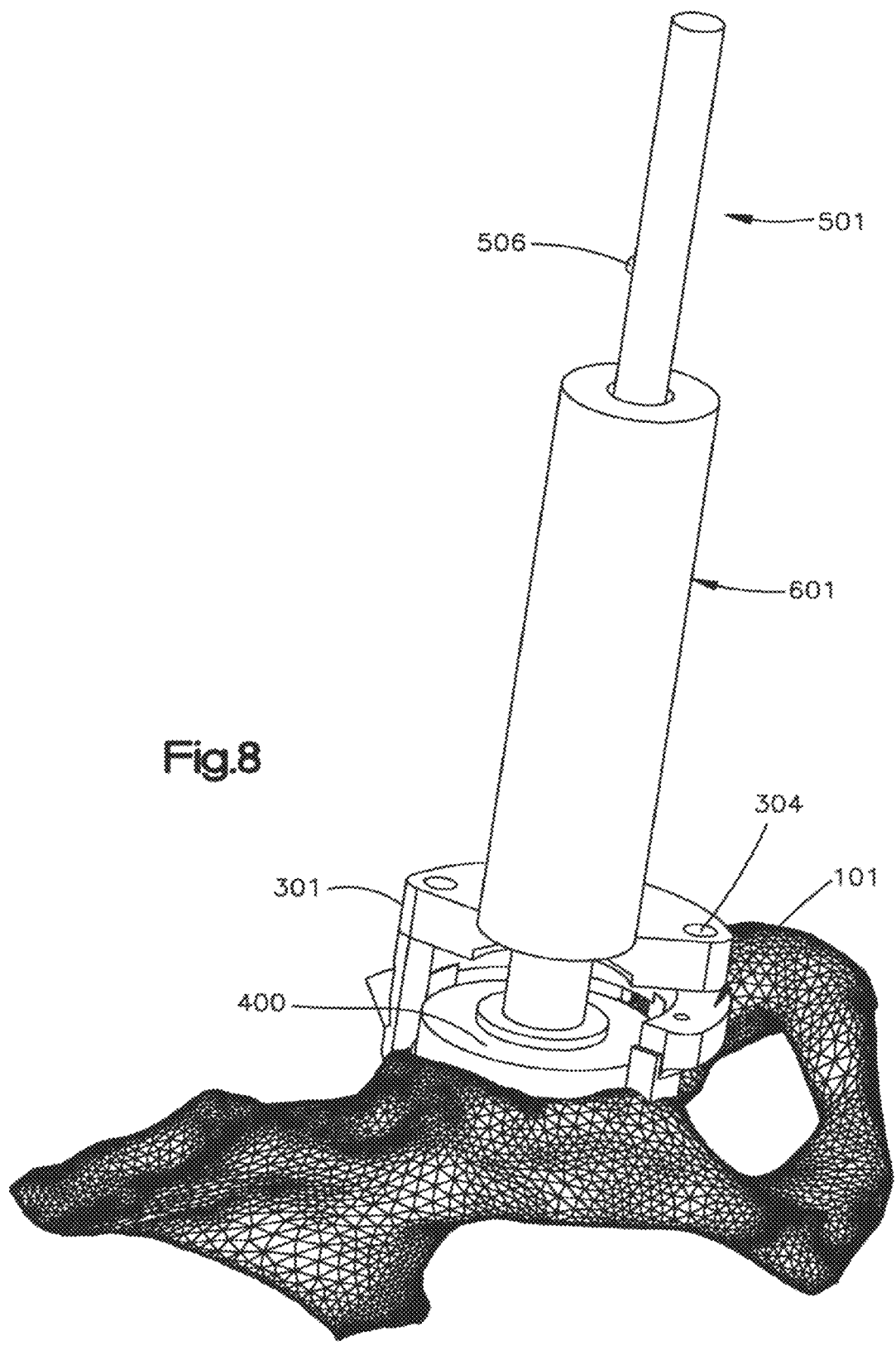
FIG. 8 is a front perspective view of a first and third guide with a reamer engaged with a hip joint according to an embodiment of the present invention.
Figure 9:
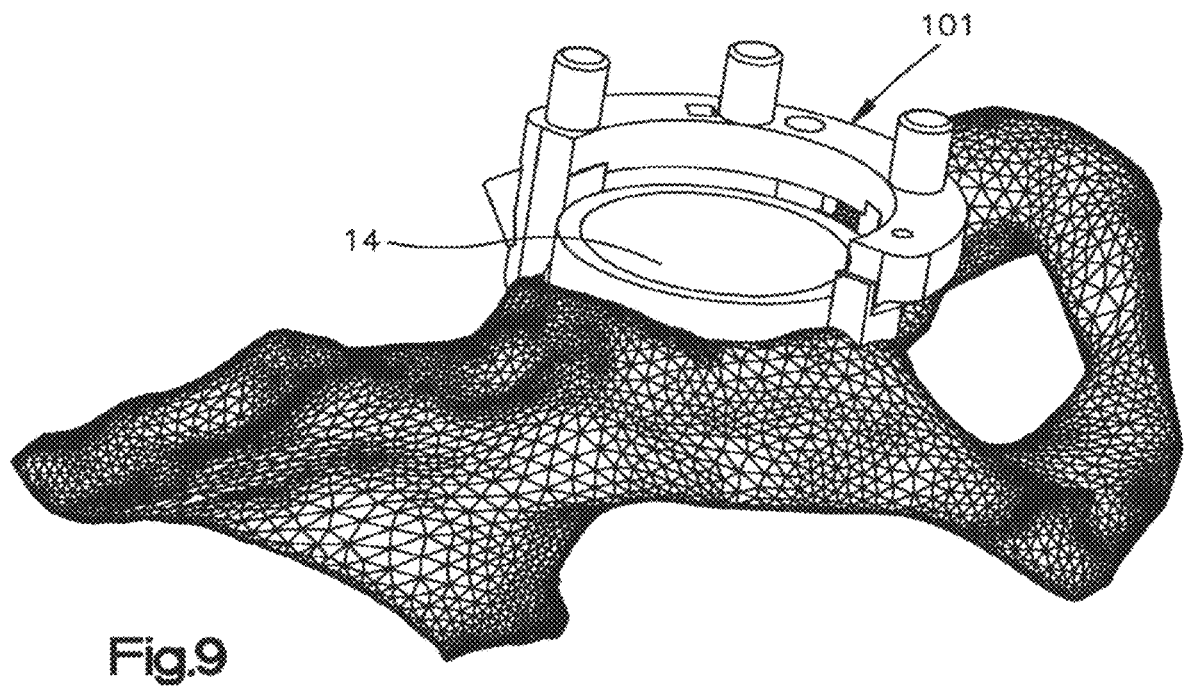
FIG. 9 is front perspective view of a first guide engaged with an acetabulum and a permanent acetabular cup in the socket of a hip joint according to an embodiment of the present invention.
Figure 10:
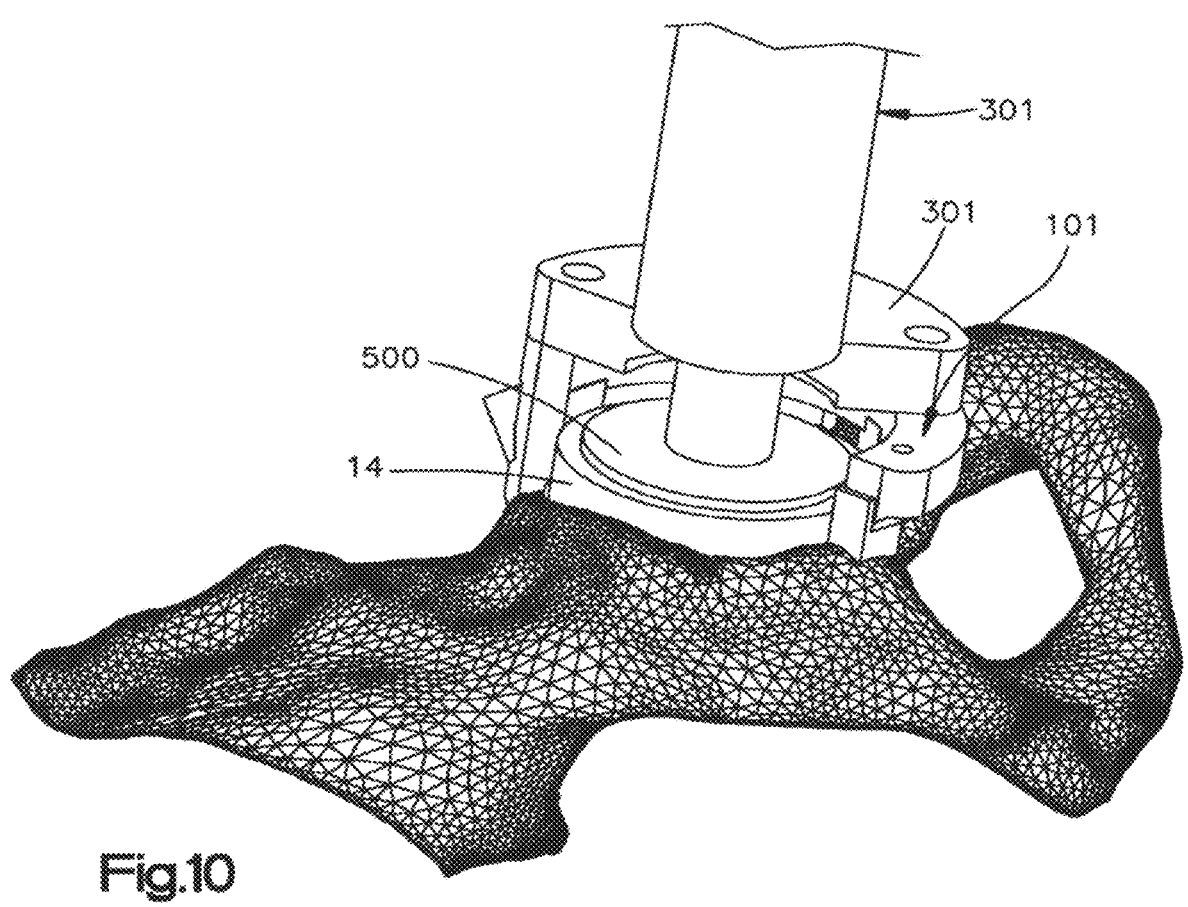
FIG. 10 is a front perspective view of a first guide and a third guide with a cup impactor to drive the permanent cup into the socket of a hip joint according to an embodiment of the present invention.

As depicted in FIGS. 6 and 7, in a preferred embodiment of the present invention, the second guide 201 is then removed to allow a reamer 501 to go into the socket of the hip joint 1. As shown in FIG. 7, the reamer shaft 502 will go through a third guide 301 and fourth guide 401. In an embodiment of the present invention, the reamer shaft 502 includes a stop 506 from the reamer shaft 502, the stop 506 being in the form of a small post, square, rectangular, or triangular projection. The stop 506 is capable of controlling the depth of the reaming. As best shown in FIG. 33, an embodiment of the present invention includes three engagement holes 304 in the third guide 301 that allow for the engagement of the three guide posts 112 (see FIG. 1) which project from the first guide 101 (see FIG. 8 for engagement of first and third guides). A person of ordinary skill in the art will readily understand that the embodiments of the present invention may include more or less than three guide posts 112 and engagement holes 304 based on the desired application of the device. FIG. 7A is a front perspective view of a third guide and fourth guide with a reamer according to an embodiment of the present invention where the reamer includes a plurality of openings 505 for bone removal during the reaming process.

When using the guide device 100 of a preferred embodiment of the present invention, once the acetabular socket is ready (i.e., enough bone has been removed), a permanent acetabular cup 14 (see FIG. 9) may be placed into the socket. Then, in an embodiment of the present invention, the third guide 301 can be used with a cup impactor 500 and mallet (not shown) to drive the cup 14 into the socket with a planned orientation (see FIG. 10).

As depicted in FIGS. 15-23, the system of the preferred embodiment of the present invention further includes at least a portion of a device 100. In a preferred embodiment of the present invention, the device 100 includes a first guide 101, a second guide 201, a third guide 301, and a fourth guide 401.

As further shown in FIGS. 24-31, in a preferred embodiment of the present invention, the first guide 101 has at least three first guide legs 102 with contact areas 104 that congruently fit with specific locations disposed both on, and directly outside of, the acetabular rim 7. In an embodiment of the present invention, at least one leg 102 is extended into and contacts the acetabular notch 8 to avoid rotation along the longitudinal axis X of the device 100. An embodiment of the present invention allows the first guide 101 to be attached on the acetabular rim 7 at a specific location. A means for fastening the first guide 101 is then used for securing the first guide 101 to the pelvic bone 5. The means for fastening the first guide 101 may include screws or the like, for example, including but not limited to bolts, dowels, pins, or the like inserted through holes 108, 109. The screws are able to penetrate the first guide legs 102 to fix the first guide 101 tightly onto the acetabulum 4. The first guide 101 of a preferred embodiment of the present invention also includes at least three first guide posts 112 that can interlock to other fixtures (such as the third guide 301 in a preferred embodiment of the present invention).

In a preferred embodiment of the present invention, the second guide 201 includes second guide legs 202 that enable the second guide 201 to engage the pelvic bone 5. The second guide 201 also includes a second guide rim 204 that aligns with the first guide rim 110 having the shape of a semi-circular ring to form a tight and stable connection. The second guide 201 may further include a connecting member 206 that cooperates with an alignment hole 114 on the first guide 101. The second guide 201 further stabilizes the device 100 such that it is unable to move (any little movement will greatly affect the accuracy of the reaming and placement of the cup 14 of an implant 3). In a preferred embodiment of the present invention, the third guide 301 (and fourth guide 401) includes a tube 302 (and 402) that guides the reamer shaft 502 of a reamer 501 and allows the reamer 501 to remove the socket surface in a precise predetermined manner. In a preferred embodiment of the present invention, the fourth guide 401 also includes a mechanism (length of the tube 402) to control the depth of reaming as well as the position and orientation of the cup 14 of the implant 3. This reamer shaft preferably includes a stop 506 or the like.

The preferred sequence of using the device 100 includes: putting guides 101 and 201 together; attaching them onto the right place of the acetabulum 1; applying screws through holes 108, 109 on first guide 101 to fix the first guide 101 onto the acetabulum 1; removing guide 201; connecting guide 301 with guide 401, putting the reamer 501 through guides 301 and 401; and connecting guide 301 with guide 101 to ream the acetabulum 1.

The device 100 preferably includes guides 101, 201, 301, 401, and reamer 501. The combination of the guides 101, 201, 301, and 401 ensures that the socket surface reaming and cup placement are done according to the computer-based optimal surgical plan according to an embodiment of the present invention.

The embodiments of the present invention therefore include custom-fit guides 101, 201, 301, 401 that are included in a main device 100 for use in THA surgery. The custom-fit surgical guides 101, 201, 301, 401 are designed to improve reaming the acetabular socket 11 and assist in placing the implant 3. Compared to traditional freehand THA and MIS surgery known in the art, the surgical guide system 1 of the embodiments of the present invention can achieve easy, accurate, reproducible, and consistent cup 14 placement. In other words, the clinical outcomes are predictable and more reliable when using the embodiments of the present invention. Compared to image guided navigation surgery known in the art, the device 100 of the embodiments of the present invention has comparable accuracy and consistency, but lower instrument costs and shorter operative time. Additionally, manufacturing of the device 100 of the embodiments of the present invention is relatively easy and cost effective.

A preferred embodiment of the present invention includes at least three first guide legs 102 with a small footprint, where the contact areas 104 are on or close to the acetabular rim 7. Therefore, this embodiment can avoid the over-removal of soft tissue and the possibility of inaccurate guide positioning. The third guide 301 and fourth guide 401 connect with the reamer 501 in a preferred embodiment of the present invention and can be easily installed or uninstalled onto the first guide 101 through the first guide posts 112. In an embodiment of the present invention, the guides 101, 201, 301, 401 are small and do not include a full circle. The guides 101, 201, 301, 401 also avoid confliction with the femur 12 and soft tissues around the acetabular rim 4. The embodiments of the present invention are more practical than designs of the prior art.

As described herein, the embodiments of the present invention include a patient-specific surgical guide system. Further, as described herein, the embodiments of the present invention include a device 100. Moreover, as described herein, the embodiments of the present invention include a method of reaming and placing an implant 3 during THA surgery. Therefore, the embodiments of the present invention include a device, system, and method of THA surgery.

A system and method of using the device 100 according to the embodiments of the present invention will now be more fully described.

The device 100 of the embodiments of the present invention is designed to solve the problem of improper position and orientation of a prosthetic cup 14 of a THA implant 3. A problem with THA surgery is that surgeons have problems obtaining proper position and orientation of the cup 14 in three dimensions. In other words, the cup 14 may be placed in the hip 1 in an off position or the orientation is a little too horizontal, a little too forward, a little too backward, or too vertical. It is difficult with a relatively small incision to know exactly what the proper position and orientation should be for many surgeons.

The embodiments of the present invention include a device 100 that is created using data obtained from a CT or MRI scan of a patient's pelvis. The data obtained from the CT or MRI scan is then inputted into a computer program. Based on the bone geometry of the patient, a technician is able to provide a surgical plan and design a device 100 according to an embodiment of the present invention.

In a preferred embodiment of the present invention, the device 100 is designed using preferably at least three areas of contact on landmarks of the patient's acetabulum 1. The device 100 may be manufactured using a 3D printer, which can print the device 100 on demand, for example, in a hospital or doctor's office. One skilled in the art will recognize that the device 100 may be manufactured using alternative methods know in the art, such as stereolithography, casting, and the like.

As shown in FIGS. 24-31, in an embodiment of the present invention, the first guide 101 includes legs 102 that are located on specific bony landmarks of the pelvis 5. The first guide 101 of the embodiments of the present invention is preferably secured so that it is only able to fit into one position on the pelvic bone 5. In a preferred embodiment of the present invention, the first guide 101 is secured to the pelvis 5 using screws or the like, which fit through holes 108, 109 in first guide rim 110. The holes can be located through the legs 102 of the first guide 101. As shown in the figures, a hole may project from the side of the first guide 101, which secures the first guide 101 from the side as well as the top. The first guide 101 is preferably secured to the pelvis 5 in a manner that causes very little tissue stripping. In other words, the first guide 101 is preferably secured to the pelvis 5 using a minimalist incision.

Figure 24:
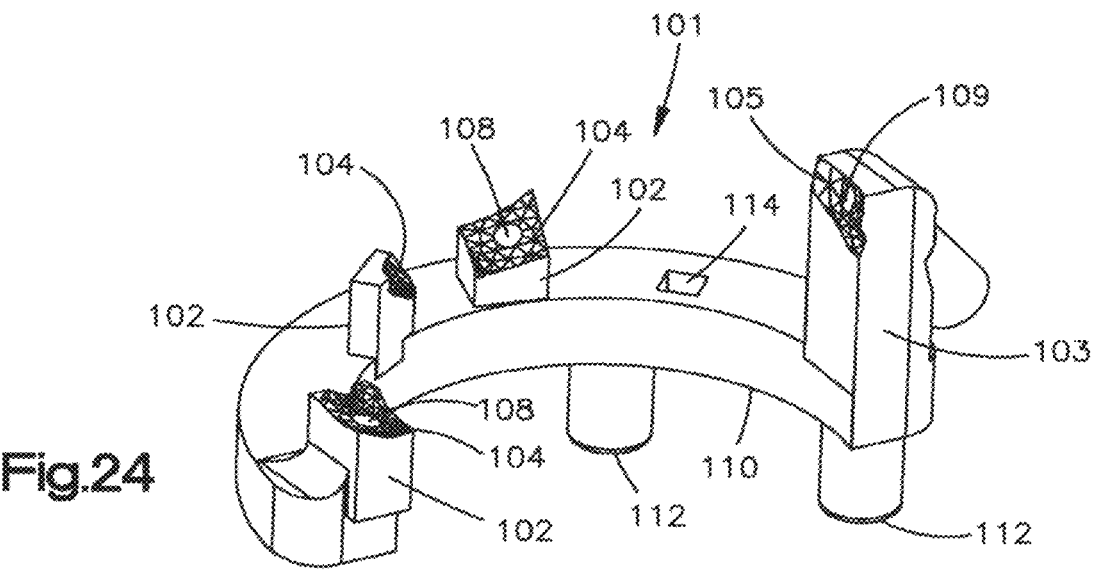
FIG. 24 is a bottom/front perspective view of a first guide according to an embodiment of the present invention.
Figure 25:
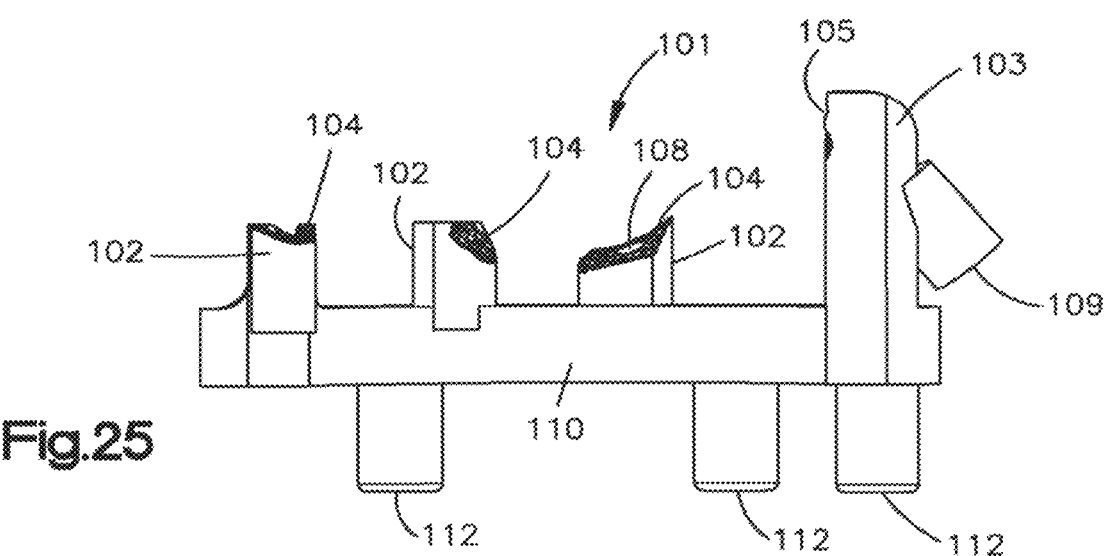
FIG. 25 is a front view of a first guide according to an embodiment of the present invention.
Figure 26:
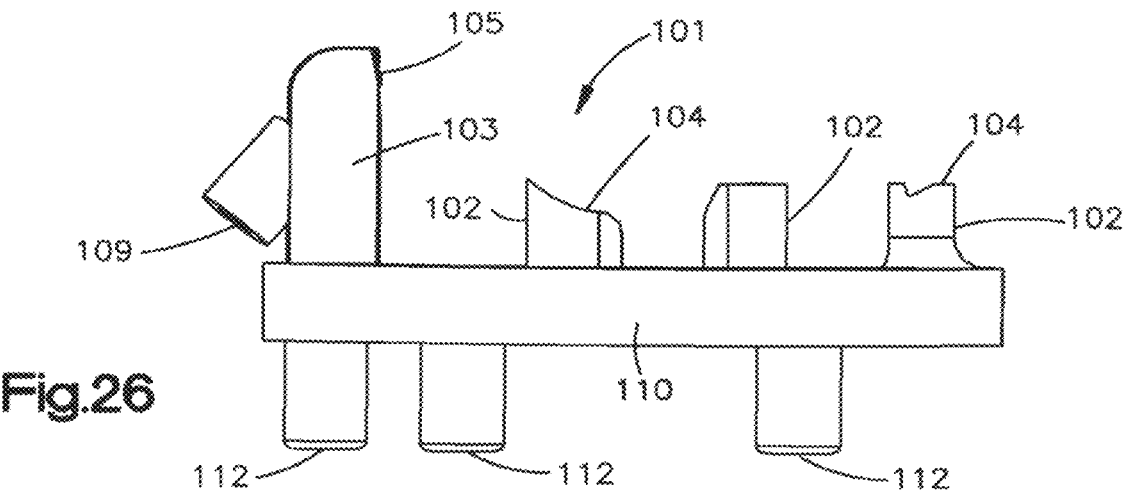
FIG. 26 is a rear view of a first guide according to an embodiment of the present invention.
Figure 28:
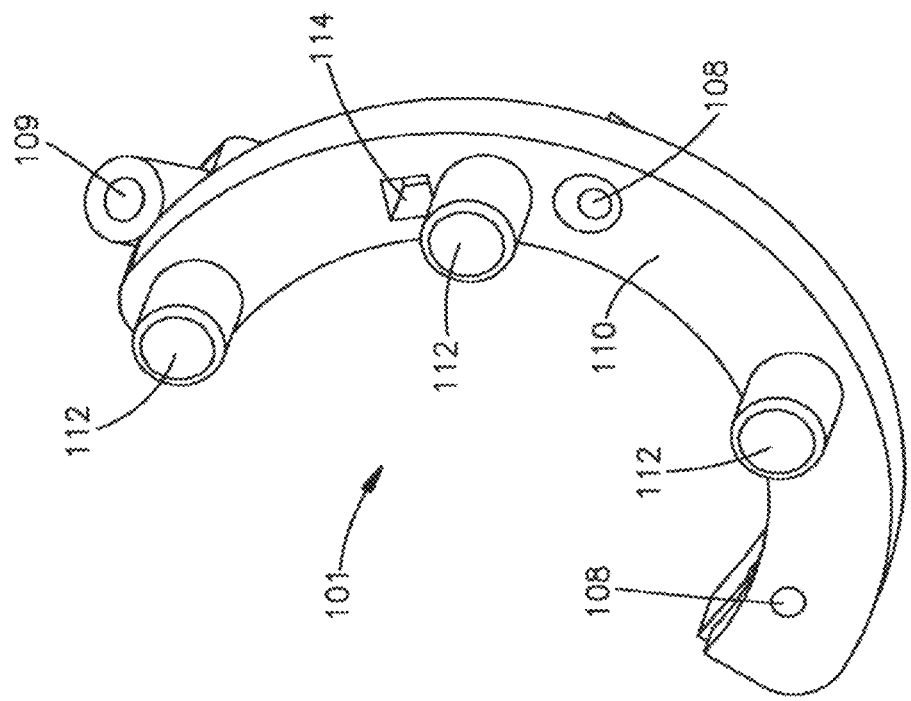
FIG. 28 is a top view of a first guide according to an embodiment of the present invention.
Figure 27:
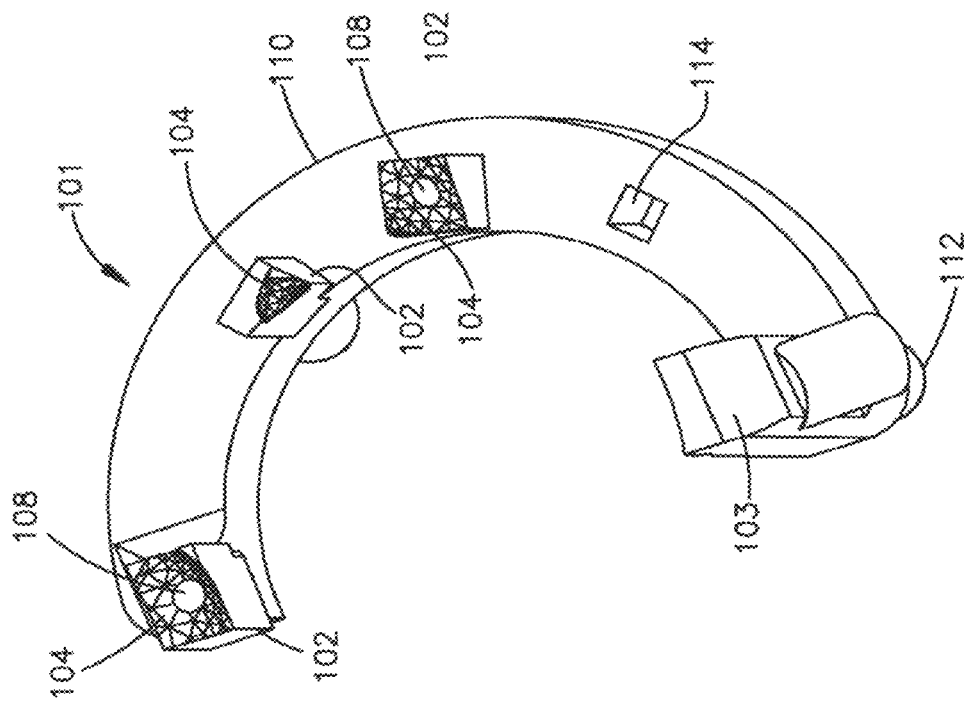
FIG. 27 is a bottom view of a first guide according to an embodiment of the present invention.
Figure 29:
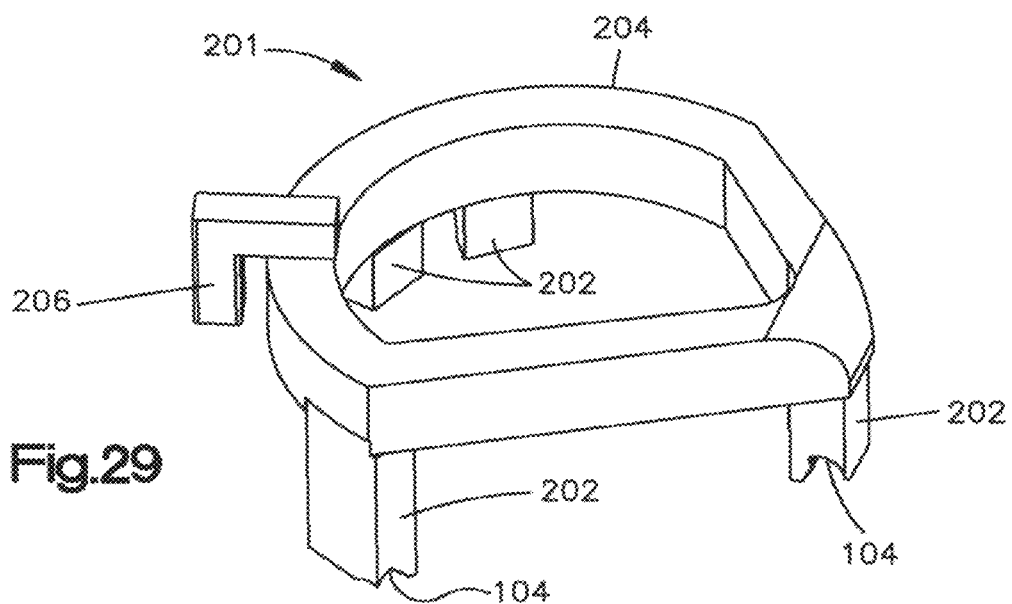
FIG. 29 is a top/side perspective view of a second guide according to an embodiment of the present invention.
Figure 30:
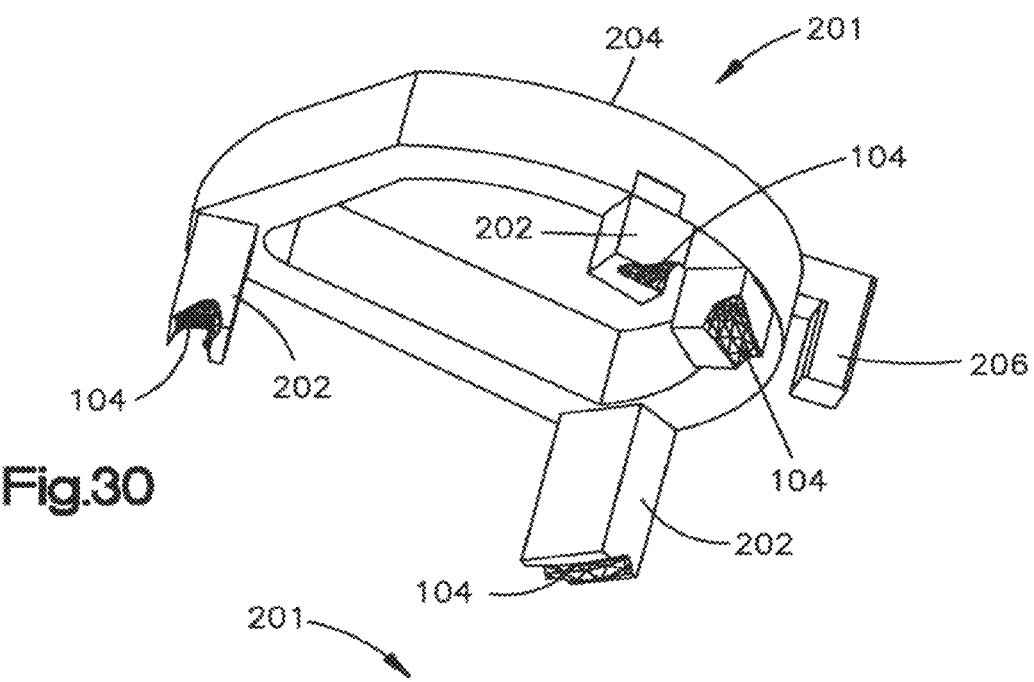
FIG. 30 is a bottom/side perspective view of a second guide according to an embodiment of the present invention.
Figure 31:
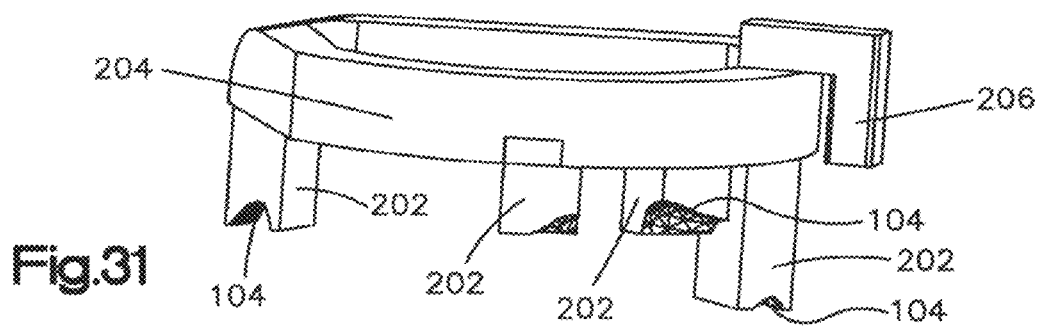
FIG. 31 is a rear view of a second guide according to an embodiment of the present invention.

FIGS. 24-27 depict the underside of the first guide 101. As shown in these figures, the contact areas 104 may be designed to interlock with the geometry of the bone to which the first guide legs 102 are to be secured. In one embodiment, if there is a long leg 103 on the first guide 101, a side screw hole can be utilized to secure the leg 103 and prevent movement of the first guide 101 when secured. The contact area 105 of the long leg 103 may be on the side of the long leg 103. In a preferred embodiment of the present invention, the shape of the first guide 101 is substantially a semi-circular shape to fit at least partially around the acetabular rim 7. One skilled in the art will understand that the first guide 101 may include different shapes, however, depending upon the patient's acetabular geometry and the desired stability of the guide 100. For example, the first guide 101 can be substantially a complete circular shape, or the first guide 101 can be substantially a quarter circular shape. As shown in FIG. 24, in a preferred embodiment of the present invention, the first guide 101 includes an alignment hole 114 for receiving connecting member 206 of the second guide 201 as shown in FIG. 29.

In a preferred embodiment of the present invention as shown in FIGS. 28-31, the second guide 201 engages the first guide 101 by fitting adjacent to the first guide rim 110, and the combination of the first and second guides 101, 201 can then be properly positioned on the acetabular rim 4. The second guide 201 shown in FIGS. 29-31 includes four second guide legs 202. One skilled in the art will understand that more or less guide legs 202 may be present in an embodiment of the present invention. As shown in the figures, the legs 202 can include contact areas that are designed to interlock with the geometry of the bone to which the second guide legs 202 are to be secured. In an embodiment of the present invention, the second guide 201 also includes a second guide rim 204 and connecting member 206 that fits on top of the first guide rim 110. The second guide 201 acts as an element to maintain stability and rigidity of the device 100 in an embodiment of the present invention. The second guide legs 202 contact and rest upon the acetabular rim 7. The placement of the first and second guides 101, 201 can be a relatively quick process, taking less than five minutes to complete.

In a preferred embodiment of the present invention, once the second guide 201 is removed, a third guide 301 shown in FIGS. 32-34 then engages with the first guide 101. The third guide 301 includes a plate 307 having a top surface and a lower surface 303, where the lower surface preferably includes the engagement surface for engagement with guide 101 and first guide rim 110 by guide posts 112 going through engagement holes 304 disposed on plate 307. A person of ordinary skill in the art will readily see that the plate 307 as shown in the figures is generally flat on both surfaces but may include other surfaces or grooves therein as necessary to facilitate use of the device 100. In addition, as shown best in FIG. 33, the plate 307 includes a pie-like shape, having a first corner A in, for example purposes only, at a 6 o'clock position, and a second corner B at an approximate 10 o'clock position, thereby having an angular relationship between corners A and B between 120 and 160 degrees, with a preferred range of 135 degrees. The arc C connects corners A and B together, the arc C having a certain arc of curvature or convex shape as shown in FIG. 33. The plate 307 also includes the engagement holes 304, with each hole being preferably ⅜ inch in diameter but like other dimensions specified herein, may vary depending on the specific application and unique design for the patient. The engagement holes 304 are preferably laid out on the plate 307 as shown in FIG. 33, with two holes 304 being generally located adjacent to corners A and B, and the middle hole being generally located in the middle of the arc C, generally equidistant from the other two holes 304.

The guide 301 also includes a tube 301 having a cylindrical shape with a hollow shaft 306, the wall thickness of the tube being ¼ inch but again, the thickness may vary as understood by a person of ordinary skill in the art. The outside diameter of the tube is preferably several inches. As best shown in FIG. 34, the tube includes a top open end 309 and bottom end 310 connected to the plate 307. The preferred length of the tube 302 is 3 inches but this distance may vary as understood by a person of ordinary skill in the art and required depth of reaming. As shown in FIG. 34, the tube 302 and plate 307 normally are provided as one unit but in certain embodiments they may be provided separately and attached before use in ways understood by a person of ordinary skill in the art. The bottom end 310 of the tube 302 is preferably attached on the top surface of plate 307 but may be connected on an interior circumference of the plate 307, where the bottom end 310 is flush with the bottom surface 303 of the plate 307. As shown in FIGS. 32-34, the interior shaft at the first end 309 of the tube 302 preferably includes at least two square or rectangular projections 311, each projection having a length of ⅕ inch and a width of ⅙ inch understanding of course, that the projections can take the shape of an oval, circular or other design as understood by a person of ordinary skill in the art. The projections 311 are also preferably disposed approximately 180 degrees apart from each other but this can vary as well depending on patient and device 100 needs.

In another embodiment of the present invention, the third guide 301 engages with first guide 101. The third guide 301 includes an engagement area 303 with engagement holes 304 that engage with the first guide posts 112 disposed on the first guide rim 110 of the first guide 101. One skilled in the art will understand that more or less guide posts 112 and engagement holes 304 may be present in an embodiment of the present invention. Moreover, one skilled in the art will understand that alternative means for engaging the first and third guides 101, 301 may be present in an embodiment of the present invention, for example, including but not limited to snap-fit connections, pins, bolts, screws, hooks, latches, or the like. In a preferred embodiment of the present invention, the third guide 301 includes a cylinder or tube 302 that has a hollow shaft 306 in which a reamer shaft 502 can be placed to properly align and guide a reamer 501. In other words, in a preferred embodiment of the present invention, the tube 302 and shaft 306 act as a cylindrical bearing that controls the alignment of the reamer 501.

Figure 35:
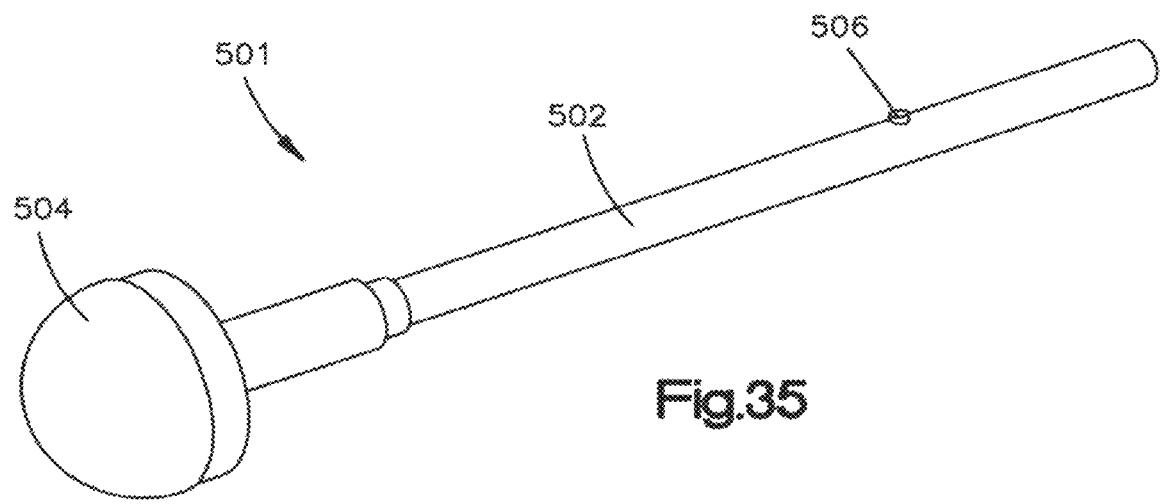
FIG. 35 is a bottom/side perspective view of a reamer according to an embodiment of the present invention.
Figure 36:
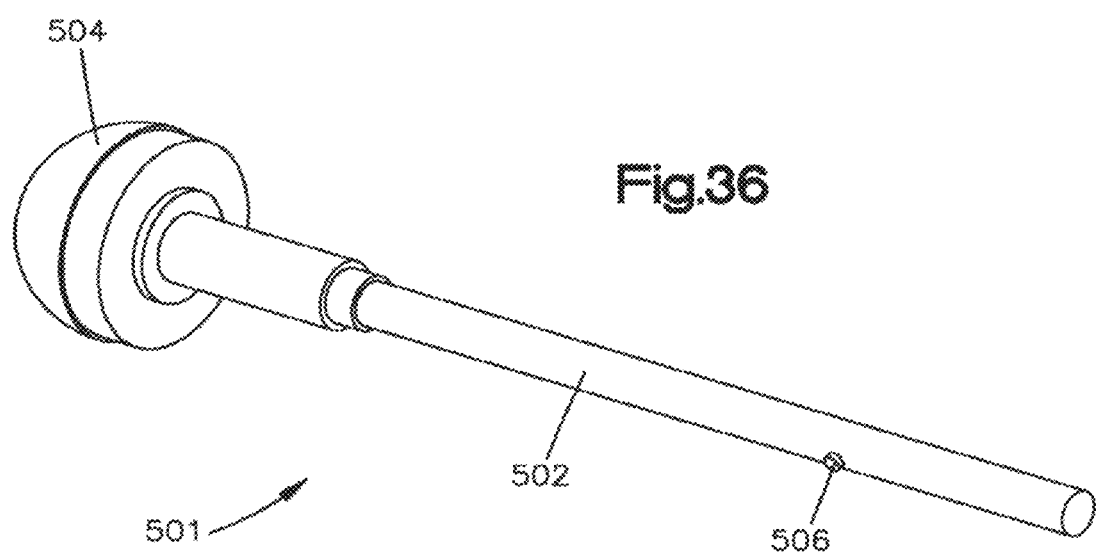
FIG. 36 is a top/side perspective view of a reamer according to an embodiment of the present invention.

For reference, a reamer 501 is depicted in FIGS. 35 and 36. The reamer 501 includes a reamer shaft 502 and a reamer head 504 with embodiment of the reamer 501 having holes as shown in FIG. 7. The reamer shaft 502 may include a stop 506 that prevents the reamer shaft 502 from penetrating into the guide 100 too far and thereby allows the reamer head 504 to achieve a proper depth in the acetabulum 4. As shown in FIGS. 35 and 36, the reamer head 504 has a bowl-like shape known in the art, having different dimensions based on the patient-specific reaming requirements.

Figure 37:
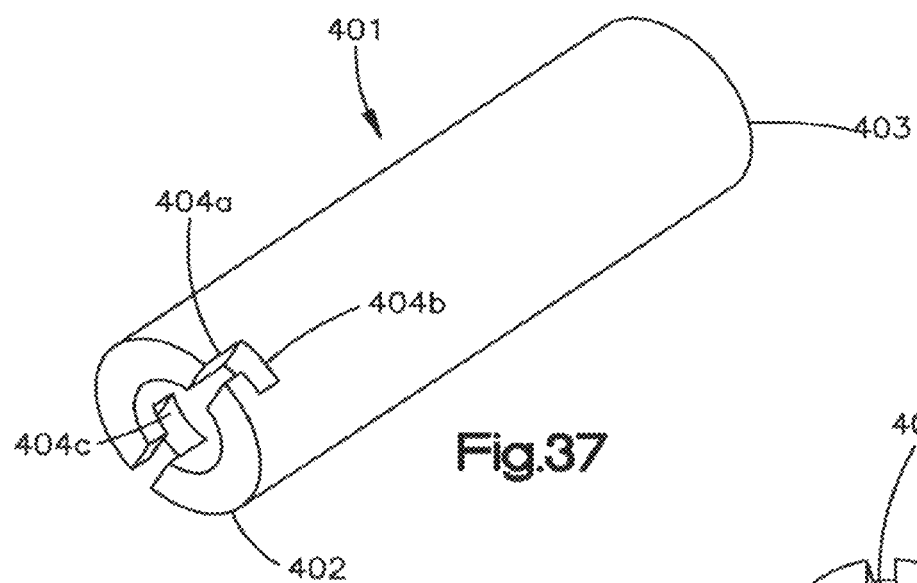
FIG. 37 is a bottom/side perspective view of a fourth guide according to an embodiment of the present invention, showing the side of the fourth guide that connects to the third side.
Figure 38:
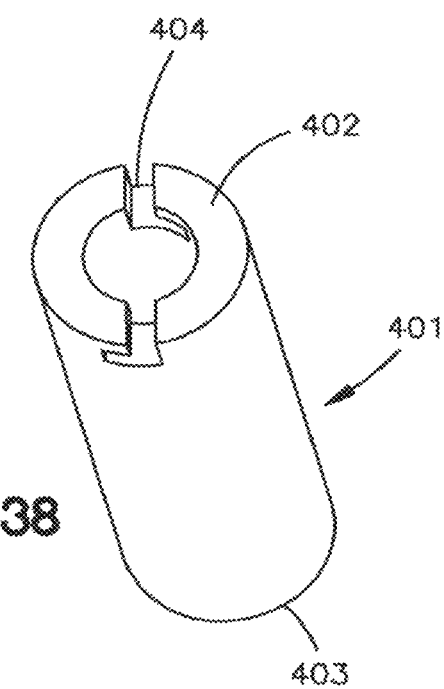
FIG. 38 is a bottom view of a fourth guide according to an embodiment of the present invention, showing the side of the fourth guide that connects to the third guide.
Figure 39:
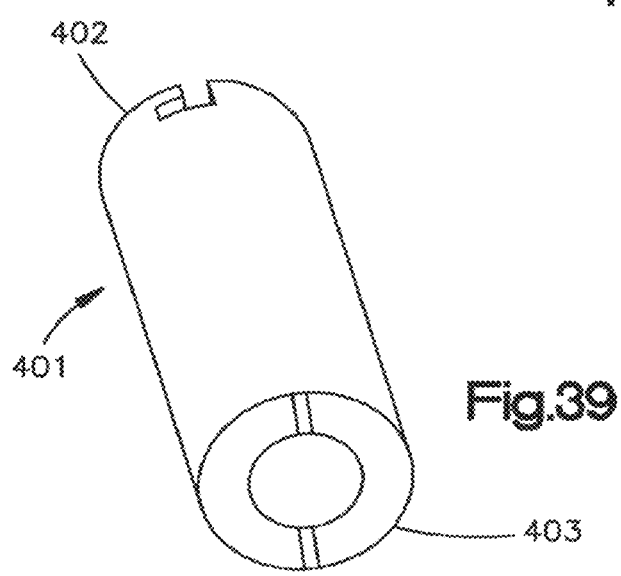
FIG. 39 is a top/side perspective view of a fourth guide according to an embodiment of the present invention.

FIGS. 37-39 show preferred embodiments of the fourth guide 401. As shown, the fourth guide includes a generally cylindrical tube having a bottom end 402 for connection to the third guide 301 and specifically for connection to the top end 309. As best shown in FIGS. 37 and 38, the bottom end 402 of the tube 401 includes preferably correspond "L" shaped cutouts in the tube, where each L shape includes a vertical leg 404a, horizontal leg 404b, and in the other side, vertical leg 404a and horizontal leg 404c, with horizontal legs 404b and 404c extending in opposite directions for protrusions 311 from third guide 301 to engage the legs 404a and to lock the fourth guide 401 onto the third guide 301 when the protrusions 311 engage horizontal legs 404b and 404c in the engagement position.

A person of ordinary skill in the art will readily understand that guide 401 can be a standard length metallic tube as part of a regular surgical instrument, while guides 101, 201 and 301 are patient specific and are preferably made by a 3D printer or like.

FIG. 40 is a perspective view of a reamer 501, third guide 301 and fourth guide 401 according to an embodiment of the present invention including a dashed line that shows how these members are preferably connected together. FIG. 41 is a perspective view of an assembled reamer 501, third guide 301 and fourth guide 401 according to an embodiment of the present invention. In these figures, guides 301 and 401 are shown as separate, independent components with unique designs. However, the embodiments of the present invention also include a design shown in FIG. 8 where the third guide 301 and fourth guide 401 as provided as one member 601.

Figure 42:
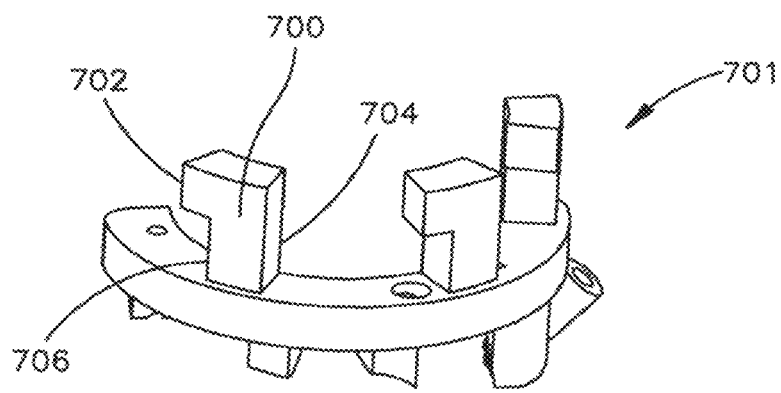
FIG. 42 is a top/front perspective view of a first guide according to another embodiment of the present invention, different from the embodiment shown in FIG. 1.

FIG. 42 is a top/front perspective view of a first guide 701 according to another embodiment of the present invention, different from the embodiment shown in FIG. 1. In FIG. 1, three guide posts 112 project from the first guide 101 and engage circular holes 304 shown in FIG. 8 for engagement of the first and third guides. In FIG. 42, the protrusions 700 include inverted "L-shaped" members having a vertical leg 704 and horizontal leg 702. The size and dimension of these members 700 vary based on a patient's needs but may include several inches in the vertical and horizontal direction. In a preferred embodiment, FIG. 42 shows the horizontal leg 702 of each of the L-shaped members 700 pointing in the same clockwise direction. However, a person of ordinary skill in the art will appreciate that other embodiments include L-shaped members 700 with horizontal legs 702 pointing in different directions. The L-shaped members 700 have inner and outer surfaces that are preferably concave or include a certain arc that corresponds to the interior arc/shape of the first guide.

Figure 43:
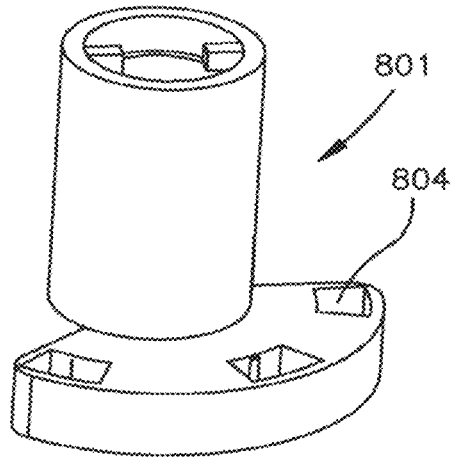
FIG. 43 is a front/top perspective view of a third guide according to another embodiment of the present invention, different from the embodiment shown in FIGS. 32-34.

FIG. 43 is a front/top perspective view of a third guide 801 according to another embodiment of the present invention, different from the embodiment shown in FIGS. 32-34. The third guide 801 shown in FIG. 43 includes many of the same features shown in FIGS. 32-34 and as described above. However, the openings 804 are generally rectangular and shaped in a way to match the design of the horizontal section 702 of the L-shaped member 700 shown in FIG. 42 including having similar concavities/internal arcs of curvature/shapes to match the horizontal sections 702 of the L-shaped members 700.

Figure 44:
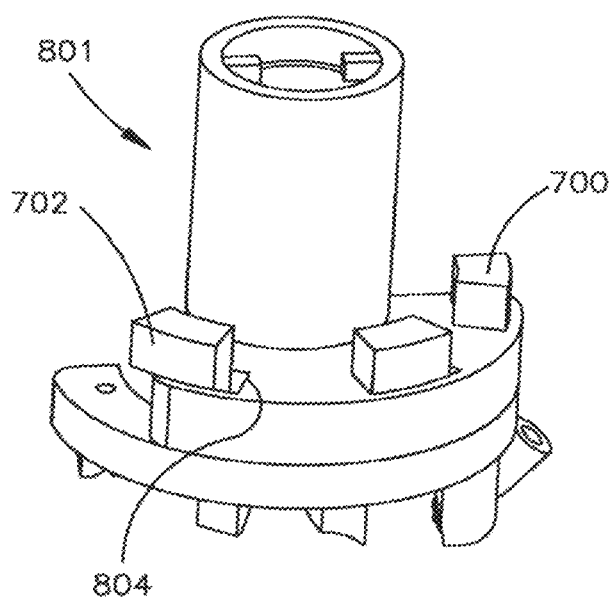
FIG. 44 is a front/top perspective view of the first guide shown in FIG. 42 connected to the third guide shown in FIG. 43.

FIG. 44 is a front/top perspective view of the first guide 701 shown in FIG. 42 connected to the third guide 801 shown in FIG. 43. As shown in FIG. 44, the horizontal sections 702 of the L-shaped members 700 protrude through the openings 804 in the third guide. The horizontal plate of the third guide 801 is then moved counterclockwise to lock or secure the third guide 801 to the first guide 701.

Based on the previously taken CT scan, a surgeon preferably could ream a pelvis 5 in one step. Therefore, the embodiments of the present invention can allow a surgeon to avoid reaming by starting small and getting larger and larger with each iteration of reaming. The preferable one step approach to reaming that is possible through the use of the device 100 according to the embodiments of the present invention will save time and increase accuracy. A person skilled in the art will understand that a system using the device 100 according to the embodiments of the present invention may include single step reaming, two step reaming, or more if so desired.

Once the acetabulum 4 is reamed to the desired depth and shape, then the cup 14 of an implant 3 may be inserted into the acetabulum 4. This typically occurs when the reaming causes the bone to begin bleeding which allows fixation of a porous coated implant cup.

The device 100 according to an embodiment of the present invention is also capable of controlling the orientation of the cup 14 of the implant 3. In other words, the cup 14 of a permanent implant 3 can be oriented and positioned by the device 100. This is desirable because, once the acetabulum 4 is reamed, it may be difficult to properly orient the cup 14. In an embodiment of the present invention, the third guide 301 and fourth guide 401 are preferably removed from the first guide 101 in order to release the reamer 501 and place a cup impactor 500. Then the third guide 301, fourth guide 401 and cup impactor 500 are assembled with the first guide 101 again. A mallet (not shown) will drive the cup 14 of the implant 3 in the acetabulum 4.

In an alternate embodiment of the present invention, the second guide 201 is secured to the first guide 101 by screws or the like. In another alternate embodiment of the present invention, the second guide 201 simply fits onto the first guide 101 in a manner that creates a secure fit without any screws or the like.

The device 100 according to the embodiments of the present invention is a fairly rigid construct once it is put together (the first, second, third and fourth guides 101, 201, 301, 401 are engaged on the pelvis 5).

In an embodiment of the present invention, once the acetabulum 4 is reamed, the device 100 is removed and discarded. In an alternate embodiment of the present invention, once the cup 14 is placed, the device 100 is removed and discarded. In other words, a preferred embodiment of the present invention is individually designed for a specific patient and is therefore designed for a one-time use.

A system according to an embodiment of the present invention includes a computer program that determines where the cup 14 of an implant 3 is preferably located based on the CT or MRI scan. Then, based on this information, the depth and shape of the reaming will be determined. Once the reaming is determined, the device 100 can be designed in order to achieve the proper reaming depth and the proper alignment of the cup 14 of the implant 3.

A further embodiment of the present invention includes a stop 506 disposed on the reamer shaft 502 in order to prevent reaming to an undesired depth. Alternatively or additionally, the third guide 301 (or fourth guide 401) may include a stop that allows a reamer 501 to achieve a proper depth in an acetabulum of the pelvic bone. A stop on the third guide 301 may be an additional element (not shown), or it may be created by the length of the tube 302 itself.

In a preferred embodiment of the present invention, there are preferably at least three points of contact between the first guide 101 and the pelvis 5. However, a person of ordinary skill will recognize that alternative embodiments of the present invention may include more or less points of contact and are not limited to the points of contact shown in the figures. In a preferred embodiment of the present invention, there are preferably at least three points of contact between the second guide 201 and the pelvis 5. However, a person of ordinary skill will recognize that alternative embodiments of the present invention may include more or less points of contact and are not limited to the points of contact shown in the figures.

In a system or method of using the device 100 according to the embodiments of the present invention, multiple reamers may be used in order to achieve the desired depth and/or shape.

The device 100 according to the embodiments of the present invention may be constructed out of various materials that can be safely used in patients including, but not limited to, plastic, metal, or the like. One skilled in the art will recognize that the device 100 is not limited to being constructed out of the materials referenced herein.

The system and method of the embodiments of the present invention includes the steps of taking a scan of a person's hip joint 1, using computer software to determine the proper location and orientation of the cup 14 of an implant 3 and the depth and shape of the reaming necessary, designing a device 100 as described herein, and using the device 100 to perform the reaming and/or placement of the cup 14 of the implant 3. The step of designing a device 100 as described herein may include using computer software to determine the ideal size, shape, and points of contact. The device 100 may then be created on demand using a 3D printer.

The embodiments of the present invention may significantly improve the precision of reaming and/or cup 14 positioning.

In an embodiment of the present invention, the second guide is integral with the first guide.

In a preferred embodiment of the present invention, the first guide 101 is aligned onto the pelvis 5 with assistance from the second guide 201. In this preferred embodiment, the second guide 201 is removed before the third guide 301 is engaged with the first guide 101. In an alternate embodiment of the present invention, the second guide 201 remains engaged with the first guide 101 when the third guide 301 is engaged with the first guide 101.

The system for designing the device 100 according to the embodiments of the present invention may be used for different surgeries besides THA, such as total knee arthroplasty (TKA), total shoulder arthroplasty (TSA), or similar.

We claim:

1. A method of performing total hip arthroplasty surgery comprising:
    (a) determining a size and placement of an acetabular implant based on a computer model of at least one of a patient's pelvis and a patient's femur performed with a diagnostic scan; and
    (b) positioning an acetabular reaming and guide device based on the determined size and placement, the device comprising:
        a first guide member comprising:
            a substantially semi-circular ring having a top surface and a bottom surface,
            a plurality of first guide legs protruding vertically downward from the lower surface of the semi-circular ring, the first guide legs including a contact area disposed on the open end of the first guide leg;
            a plurality of holes disposed on the ring,
            a plurality of protrusions extending vertically upward from a top surface of the ring, and
        a second guide member comprising:
            an arc having an arc of curvature substantially similar to the semi-circular ring, the arc having a top surface and bottom surface
            first and second horizontal brackets connecting ends of the arc and being connected thereto at a termination point,
            a plurality of second guide legs protruding vertically from either the lower surface of the arc, first or second horizontal brackets; and
        means for connecting the second guide member to the first guide member,
        a third guide member comprising:
            a cylindrical first tube; and
            a horizontal plate connected to the tube having a top surface and a lower surface, wherein the lower surface includes the engagement surface for engagement with the first guide member; and
            a plurality of holes disposed on the plate,
            wherein the plurality of protrusions protruding from the top surface of the semi-circular ring are capable of entering the plurality of holes disposed on the plate to engage the first guide member with the third guide member;
        a fourth guide member comprising:
            a cylindrical second tube capable of being connected to the first tube, wherein the outside diameter of the second tube is less than the inside diameter of the first tube to allow engagement; and means for engaging the second tube to the first tube.

2. The method according to claim 1, further comprising: reaming at least one of the patient's pelvis and the patient's femur based upon the positioning of the acetabular reaming and guide device.

3. The method according to claim 2, wherein reaming at least one of the patient's pelvis and the patient's femur based upon the positioning of the acetabular reaming and guide device includes removing bone with a pre-determined orientation and depth.

4. The method of claim 3, wherein reaming at least one of the patient's pelvis and the patient's femur includes removing at least one of diseased bone and cartilage.

5. The method of claim 3, wherein reaming at least one of the patient's pelvis and the patient's femur includes sizing a new socket for the implant.

6. The method according to claim 1, further comprising: affixing the acetabular reaming and guide device onto an area of bone of at least one of the patient's pelvis and the patient's femur.

7. The method according to claim 1, further comprising: placing the implant on at least one of the patient's pelvis and the patient's femur based on the position of the acetabular reaming and guide device.

8. The method according to claim 1, further comprising: securing the first guide member to the patient's hip joint.

9. The method according to claim 1, further comprising: contacting and maintaining the second guide member at pre-determined areas on an acetabular rim of the patient.

10. The method according to claim 1, further comprising: removing the second guide member to allow further placement of a reamer into a socket of a hip joint of the patient.

11. The method according to claim 1, further comprising: placing an acetabular cup into a socket of the patient's pelvis based upon the position of the acetabular reaming and guide device.

12. The method according to claim 1, further comprising: inserting screws through the plurality of holes disposed on the ring to secure the first guide member to the patient's hip.

13. The method according to claim 1, further comprising: creating the computer model of at least one of a patient's pelvis and a patient's femur, wherein the computer model includes a three-dimensional computer model, and the diagnostic scan includes at least one of a CT and MRI scan.

14. The method according to claim 1, further comprising: extending the first guide member and contacting an acetabular notch of the patient; and attaching the first guide member to an acetabular rim of the patient to avoid rotation along a longitudinal axis of the device.

15. The method according to claim 1, wherein positioning an acetabular reaming and guide device includes:

assembling the first guide member and the second guide member;

attaching the first guide member and the second guide member to an acetabulum of the patient;

inserting screws through holes on the first guide member to fix the first guide member onto the acetabulum;

removing the second guide member;

connecting the third guide member with the fourth guide member;

inserting a reamer through the third guide member and the fourth guide member; and connecting the third guide member with the first guide member for reaming the acetabulum.

16. A method of performing total hip arthroplasty surgery comprising:

(a) determining a size and placement of an acetabular implant based on a computer model of at least one of a patient's pelvis and a patient's femur performed with a diagnostic scan; and (b) positioning an acetabular reaming and guide device based on the determined size and placement, the device comprising:

a first guide member comprising:
a substantially semi-circular ring having a top surface and a bottom surface,
a plurality of first guide legs protruding vertically downward from the lower surface of the semi-circular ring, the first guide legs including a contact area disposed on the open end of the first guide leg;
a plurality of holes disposed on the ring,
a plurality of protrusions extending vertically upward from a top surface of the ring, and a third guide member comprising:
a cylindrical first tube; and
a horizontal plate connected to the cylindrical first tube having a top surface and
a lower surface, wherein the lower surface includes the engagement surface for engagement with the first guide member; and
a plurality of holes disposed on the plate,
wherein the plurality of protrusions protruding from the top surface of the semi-circular ring are capable of entering the plurality of holes disposed on the plate to engage the first guide member with the third guide member;
a fourth guide member comprising:
a cylindrical second tube capable of being connected to the first tube, wherein the outside diameter of the second tube is less than the inside diameter of the first tube to allow engagement; and
means for engaging the second tube to the first tube.

17. A method of performing total hip arthroplasty surgery comprising:

(a) determining a size and placement of an acetabular implant based on a computer model of at least one of a patient's pelvis and a patient's femur performed with a diagnostic scan; and (b) positioning an acetabular reaming and guide device based on the determined size and placement, the device comprising:

a first guide member comprising:
a substantially semi-circular ring having a top surface and a bottom surface,
a plurality of first guide legs protruding vertically downward from the lower surface of the semi-circular ring, the first guide legs including a contact area disposed on the open end of the first guide leg;
a plurality of holes disposed on the ring,
a plurality of protrusions extending vertically upward from a top surface of the ring, and
a third guide member comprising:
a cylindrical first tube; and
a horizontal plate connected to the cylindrical first tube having a top surface and a lower surface, wherein the lower surface includes the engagement surface for engagement with the first guide member; and a plurality of holes disposed on the plate, wherein the plurality of protrusions protruding from the top surface of the semi-circular ring are capable of entering the plurality of holes disposed on the plate to engage the first guide member with the third guide member;

a fourth guide member comprising:

a cylindrical second tube capable of being connected to the first tube, wherein the outside diameter of the second tube is less than the inside diameter of the first tube to allow engagement;

means for engaging the second tube to the first tube, wherein the plurality of first guide legs have the same or different lengths depending on the patient's specific needs, and wherein the contact areas include flat, concave, and convex shapes to fit a patient's hip joint.

* * * * *